United States Patent
Holmes et al.

(10) Patent No.: US 10,561,642 B2
(45) Date of Patent: *Feb. 18, 2020

(54) TREATMENT OF ZIKA VIRUS INFECTIONS USING ALPHA-GLUCOSIDASE INHIBITORS

(71) Applicant: FLORIDA STATE UNIVERSITY RESEARCH FOUNDATION, INC., Tallahassee, FL (US)

(72) Inventors: Eric Holmes, Tallahassee, FL (US); Gary Ostrander, Tallahassee, FL (US)

(73) Assignee: FLORIDA STATE UNIVERSITY RESEARCH FOUNDATION, INC., Tallahassee, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/856,377

(22) Filed: Dec. 28, 2017

(65) Prior Publication Data

US 2018/0117018 A1    May 3, 2018

Related U.S. Application Data

(63) Continuation of application No. PCT/US2017/030653, filed on May 2, 2017.

(Continued)

(51) Int. Cl.
*A61K 31/445*    (2006.01)
*A61K 31/44*    (2006.01)
(Continued)

(52) U.S. Cl.
CPC ............ *A61K 31/437* (2013.01); *A61K 9/127* (2013.01); *A61K 31/33* (2013.01); *A61K 45/06* (2013.01);
(Continued)

(58) Field of Classification Search
CPC ............................ A61K 31/437; A61K 31/445
(Continued)

(56) References Cited

U.S. PATENT DOCUMENTS

| 4,065,562 A | 12/1977 | Ohata et al. |
| 4,182,767 A | 1/1980 | Murai et al. |

(Continued)

FOREIGN PATENT DOCUMENTS

| EP | 0202661 | 8/1993 |
| WO | WO 90/01319 | 2/1990 |

(Continued)

OTHER PUBLICATIONS

Faye et al. "One step RT-PCR for detection of Zika virus," J. Clinical Virology, 2008, vol. 43, pp. 96-101.*

(Continued)

*Primary Examiner* — Shengjun Wang
(74) *Attorney, Agent, or Firm* — Saliwanchik, Lloyd & Eisenschenk

(57) ABSTRACT

The present invention concerns the use of castanospermine or other alpha-glucosidase inhibitors for the treatment or prevention of Zika virus infections. Aspects of the invention include methods for treating or preventing Zika virus infection by administering an alpha-glucosidase inhibitor (e.g., an alpha-glucosidase I inhibitor) to a subject in need thereof; methods for inhibiting a Zika virus infection in a cell in vitro or in vivo; pharmaceutical compositions; packaged dosage formulations; and kits for treating or preventing Zika virus infection.

20 Claims, 4 Drawing Sheets

Related U.S. Application Data

(60) Provisional application No. 62/330,663, filed on May 2, 2016.

(51) Int. Cl.
| | |
|---|---|
| A61K 31/437 | (2006.01) |
| A61K 31/33 | (2006.01) |
| C07D 401/02 | (2006.01) |
| A61K 47/60 | (2017.01) |
| A61P 31/14 | (2006.01) |
| A61K 9/127 | (2006.01) |
| A61K 45/06 | (2006.01) |
| C12P 17/12 | (2006.01) |

(52) U.S. Cl.
CPC ............ A61K 47/60 (2017.08); A61P 31/14 (2018.01); C07D 401/02 (2013.01); C12P 17/12 (2013.01); Y02A 50/391 (2018.01)

(58) Field of Classification Search
USPC ................................................. 514/315, 299
See application file for complete search history.

(56) References Cited

U.S. PATENT DOCUMENTS

| | | | |
|---|---|---|---|
| 4,278,683 A | 7/1981 | Stoltefuss et al. | |
| 4,533,668 A | 8/1985 | Shingo et al. | |
| 4,639,436 A | 1/1987 | Junge et al. | |
| 4,792,558 A | 12/1988 | Sunkara et al. | |
| 5,004,476 A | 4/1991 | Cook | |
| 5,017,563 A | 5/1991 | Liu et al. | |
| 5,043,273 A | 8/1991 | Scudder et al. | |
| 2006/0194835 A1 | 8/2006 | Dugourd et al. | |
| 2009/0252785 A1* | 10/2009 | Pollock | A61K 9/127 424/450 |
| 2013/0315861 A1* | 11/2013 | Canales | C07D 409/12 424/85.4 |
| 2015/0087688 A1* | 3/2015 | Hersel | A61K 47/48215 514/425 |
| 2017/0312257 A1 | 11/2017 | Holmes et al. | |

FOREIGN PATENT DOCUMENTS

| | | |
|---|---|---|
| WO | WO 03/006017 | 1/2003 |
| WO | WO 2006/037227 | 4/2006 |

OTHER PUBLICATIONS

Abnova catalog No. KA 1608, Alpha-Glucosidase Assay Kit, product datasheet downloaded Feb. 2018.
Abcam ab174093, Alpha-Glucosidase Activity Assay Kit (Colorimetric), product datasheet downloaded Feb. 2018.
Aguilar-Moncayo, M. et al., "Glycosidase inhibition by ring-modified castanospermine analogues: tackling enzyme selectivity by inhibitor tailoring" *Org. Biomol. Chem.*, 2009, 7(13):2738-2747.
Bernotas, R.C. and Ganem, B., "Total syntheses of (+)-castanospermine and (+)deoxynojirimycin" *Tetrahedron Letters*, 1984, 25:165-168.
Burgess, K. et al., "A route to several stereoisomers of castanospermine" *J. Org. Chem.*, 1992, 57(4):1103-1109.
Burgess, K., "Synthetic approaches to stereoisomers and analogues of castanospermine" *Tetrahedron*, 1992, 48(20):4045-4066.
Ceccon, J. et al., "Asymmetric synthesis of (+)-castanospermine through enol ether metathesis—hydroboration/oxidation" *Organic & Biomolecular Chemistry*, 2009, 7(10):2029-2031.
Chang, J. et al., "Competitive inhibitor of cellular α-glucosidases protects mice from lethal dengue virus infection" *Antiviral Res.*, 2011, 92(2):369-371.
Chang, J. et al., "Imino sugar glucosidase inhibitors as broadly active anti-filovirus agents" *Emerging Microbes and Infections*, 2013, 2(11):e77.

Courageot, M.P. et al., "Alpha-glucosidase inhibitors reduce dengue virus production by affecting the initial steps of virion morphogenesis in the endoplasmic reticulum" *Journal of Virology*, 2000, 74(1):564-572.
Elbein, A.D., "Glycosidase inhibitors as antiviral and/or antitumor agents" *Semin Cell Biol.*, 1991, 2(5):309-317, abstract.
Elbein, A.D., "Glycosidase inhibitors: inhibitors of N-linked oligosaccharide processing" *FASEB J*, 1991, 5(15):3055-3063.
Gloster, T.M. and Davies, G.J., "Glycosidase inhibition: assessing mimicry of the transition state" *Org. Biomol. Chem.*, 2010, 8(2):305-320.
Jacob, G.S., "Glycosylation inhibitors in biology and medicine" *Curr Opin Struct Biol.*, 1995, 5(5):605-611.
Kajimoto, T. and Node, M., "Inhibitors against glycosidases as medicines" *Curr Top Med Chem*, 2009, 9(1):13-33.
Kang, M.S., "Uptake and metabolism of BuCast: a glycoprotein processing inhibitor and a potential anti-HIV drug" *Glycobiology*, 1996, 6(2):206-216.
Kang, MS et al., "Castanospermine analogues: their inhibition of glycoprotein processing α-glucosidases from porcine kidney and B16F10 cells" *Glycobiology*, 1995, 5(1):147-152, abstract.
Kaskoos, R., "In-vitro α-glucosidase inhibition and antioxidant activity of methanolic extract of Centaurea calcitrapa from Iraq" *American Journal of Essential Oils and Natural Products*, 2013, 1(1):122-125.
Kaushal, G.P. et al., "Selective inhibition of glycoprotein processing enzymes. Differential inhibition of glucosidases I and II in cell culture" *J Biol Chem.*, 1988, 263(33):17278-17283.
Kim, Y.-M. et al., "Inhibitory effect of pine extract on alpha-glucosidase activity and postprandial hyperglycemia" *Nutrition*, 2005, 21(6): 756-761, abstract.
Krishnan, M.N. and Garcia-Blanco, M.A., "Targeting host factors to treat West Nile and dengue viral infections" *Viruses*, 2014, vol. 6, pp. 683-708.
Lu, Y. et al., "Loddigesiinols G-J: α-glucosidase inhibitors from Dendrobium loddigesii" *Molecules*, 2014, vol. 19, pp. 8544-8555.
McGinnes, L.W., and Morrison, T.G. "Role of carbohydrate processing and calnexin binding in the folding and activity of the HN protein of Newcastle disease virus" *Virus Res*, 1998, 53:175-185.
Mohana, S. et al., "Antiviral activities of sulfonium-ion glucosidase inhibitors and 5-thiomannosylamine disaccharide derivatives against dengue virus" *International Journal of Antimicrobial Agents*, 2012, vol. 40, No. 3, pp. 273-276.
Montefiori, D.C. et al., "Role of protein N-glycosylation in pathogenesis of human immunodeficiency virus type 1" *Proc Natl Acad Sci USA*, 1988, 85:9248-9252.
Muller, U. et al. "Functional role of type I and type II interferons in antiviral defense". *Science*, 1994, 264(5167):1918-21. Epub Jun. 24, 1994.
Nakamura, S. et al., "Homology Modeling of Human Alpha-Glucosidase Catalytic Domains and SAR Study of Salacinol Derivatives" *Open Journal of Medicinal Chemistry*, 2012, vol. 2, pp. 50-60.
Pili, R. et al., "The alpha-glucosidase I inhibitor castanospermine alters endothelial cell glycosylation, prevents angiogenesis, and inhibits tumor growth" *Cancer Res.*, 1995, 55:2920-2926.
Saul, R. et al. "Castanospermine inhibits alpha-glucosidase activities and alters glycogen distribution in animals" *Proc Natl Acad Sci USA*, 1985, 82:93-97.
Sayce, A.C. et al., "Iminosugars Inhibit Dengue Virus Production via Inhibition of ER Alpha-Glucosidases—Not Glycolipid Processing Enzymes" *PLOS Neglected Tropical Diseases*, 2016, vol. 10, Issue 3, pp. 1-22.
Tiwari, D.K. et al., "Divergent total synthesis of 1,6,8a-tri-epi-castanospermine and 1-deoxy-6,8a-di-epi-castanospermine from substituted azetidin-2-one (β-lactam), involving a cascade sequence of reactions as a key step" *Org Biomol Chem.*, 2014, 12(37):7389-7396.
Walker, B.D. et al. "Inhibition of human immunodeficiency virus syncytium formation and virus replication by castanospermine" *Proc Natl Acad Sci USA*, 1987, 84:8120-8124.

(56) References Cited

OTHER PUBLICATIONS

Warfield, K.L. et al. "Inhibition of endoplasmic reticulum glucosidases is required for in vitro and in vivo dengue antiviral activity by the iminosugar UV-4" *Antiviral Research*, 2016 (Epub Mar. 3, 2016), vol. 129, pp. 93-98.
Whitby, K. et al. "Castanospermine, a potent inhibitor of dengue virus infection in vitro and in vivo" *J Virol*, 2005, 79, 8698-8706.
Winchester, B.G. et al., "The structural basis of the inhibition of human glycosidases by castanospermine analogues," *Biochem. J.*, 1990, 269:227-231.
Wu, S.F. et al. "Antiviral effects of an iminosugar derivative on flavivirus infections" *J. Virol.*, 2002, 76:3596-3604.
Ioos, S. et al., "Current Zika virus epidemiology and recent epidemics," *Médecine et maladies infectieuses*, 2014, vol. 44, pp. 302-307.
Warfield, K.L. et al., "A Novel Iminosugar UV-12 with Activity against the Diverse Viruses Influenza and Dengue (Novel Iminosugar Antiviral for Influenza and Dengue)," *Viruses*, 2015, vol. 7, pp. 2404-2427.
Tyler, PC and Winchester, BG, "Synthesis and Biological Activity of Castanospermine and Close Analogs" Chapter 7, pp. 125-156, In: Iminosugars as Glycosidase Inhibitors: Nojirimycin and Beyond, edited by A.E. Stütz. Wiley-VCH Verlag GmbH, 1998.
Brendel, E. and Wingender, W., "Clinical Pharmacology of Glucosidase Inhibitors" Chapter 21, pp. 611-632, In: Kuhlmann J., Puls W. (eds) Oral Antidiabetics. Handbook of Experimental Pharmacology, vol. 119. Springer, Berlin, Heidelberg, 1996.
Junge, B. et al., "Chemistry and Structure-Activity Relationships of Glucosidase Inhibitors" Chapter 15, pp. 411-482, In: Kuhlmann J., Puls W. (eds) Oral Antidiabetics. Handbook of Experimental Pharmacology, vol. 119. Springer, Berlin, Heidelberg, 1996.
Krause, HP and Ahr, HJ, "Pharmacokinetics and Metabolism of Glucosidase Inhibitors" Chapter 19, pp. 541-555, In: Kuhlmann J., Puls W. (eds) Oral Antidiabetics. Handbook of Experimental Pharmacology, vol. 119. Springer, Berlin, Heidelberg, 1996.
Ploschke, HJ et al., "Analytical Methods of Determination of Glucosidase Inhibitors" Chapter 16, pp. 483-496, In: Kuhlmann J., Puls W. (eds) Oral Antidiabetics. Handbook of Experimental Pharmacology, vol. 119. Springer, Berlin, Heidelberg, 1996.
Puls, W, "Pharmacology of Glucosidase Inhibitors" Chapter 17, pp. 497-534, In: Kuhlmann J., Puls W. (eds) Oral Antidiabetics. Handbook of Experimental Pharmacology, vol. 119, 1996.
Puls, W, "General Pharmacology of Glucosidase Inhibitors" Chapter 18, pp. 535-539, In: Kuhlmann J., Puls W. (eds) Oral Antidiabetics. Handbook of Experimental Pharmacology, vol. 119, 1996.
Dowall, S. et al. "Antiviral Screening of Multiple Compounds against Ebola Virus" *Viruses*, 2016, 8(277), 17 pages.
Durantel, D. "Celgosivir, an alpha-glucosidase I inhibitor for the potential treatment of HCV infection" *Curr. Opin. Investig. Drugs*, 2009, 10(8):860-870, Abstract.
Musso, D. et al. "Potential Sexual Transmission of Zika Virus" *Emerging Infectious Diseases*, 21(2):359-361.
Shan, C. et al. "Zika Virus: Diagnosis, Therapeutics, and Vaccine" *ACS Infect. Dis.*, 2016, 2:170-172.
Veluru, C. et al. "Skin Rash During Chronic Hepatitis C Therapy" *Gastroenterology & Hepatology*, 2010, 6(5):323-325.
Currently pending claims for U.S. Appl. No. 15/584,952.

\* cited by examiner

+ZIKV-FSS13025

Castanospermine

Mock | DMSO | 100uM | 500uM | 1mM

ZIKV NS1

GAPDH

FIG. 1

| Table Analyzed | NS1 ELISA 1-300 w OL |
|---|---|
| Column C | ZIKV |
| vs. | vs. |
| Column B | C200 |
| Unpaired t test | |
| P value | 0.0035 |
| P value summary | ** |
| Significantly different (P < 0.05)? | Yes |
| One- or two-tailed P value? | Two-tailed |

TREATMENT OF ZIKA VIRUS INFECTIONS USING ALPHA-GLUCOSIDASE INHIBITORS

CROSS-REFERENCE TO RELATED APPLICATIONS

The present application is a continuation of International Application Number PCT/US2017/030653, filed May 2, 2017, which claims the benefit of U.S. Provisional Application Ser. No. 62/330,663, filed May 2, 2016, each of which is hereby incorporated by reference herein in its entirety, including any figures, tables, nucleic acid sequences, amino acid sequences, or drawings.

BACKGROUND OF THE INVENTION

Castanospermine is an inhibitor of α- and β-glucosidases (Saul, R., Ghidoni, J. J., Molyneux, R. J., et al. (1985) *Proc Natl Acad Sci USA*, 82, 93-97). Glucosidases catalyze the cleavage of individual glucosyl residues from various glycoconjugates, including complex carbohydrates and glycoproteins. Glucose residues found on high mannose glycoprotein oligosaccharides must first be cleaved before they are further processed to yield complex type oligosaccharide structures. Inhibition of glycoprotein oligosaccharide processing can affect protein trafficking and cell functions that are dependent on glycosylation, including angiogenesis (Pili, R., Chang, J., Partis, R. A., et al. (1995) *Cancer Res.*, 55, 2920-2926). Castanospermine also interferes with viral replication and infection that is dependent on glucosidase activity (Montefiori, D. C., Robinson, W. E., and Mitchell, W. M. (1988) *Proc Natl Acad Sci USA*, 85, 9248-9252; Walker, B. D., Kowalski, M., Goh, W. C., et al. (1987) Proc Natl Acad Sci USA, 84, 8120-8124).

Evidence of castanospermine's antiviral activity has been reported for Dengue virus (Whitby, K., Pierson, T. C., Geiss, B., et al. (2005) *J Virol*, 79, 8698-8706; Courageot, M-P, Frenkiel, M-P, et al. (2000) *J Virol*, 74, 564-572). Dengue virus is spread via mosquitos and results in Dengue fever, the most prevalent mosquito borne human disease. Dengue virus is an enveloped single-stranded, positive-sense RNA virus of the genus Flavivirus. The Dengue virus RNA is translated in the cytoplasm as a single polyprotein that is cleaved into three structural and seven nonstructural proteins. There are four related serotypes that are transmitted to humans primarily by two mosquitoes, *Aedes aegypti* and *Aedes albopictus*.

Assembly of the Dengue virus in infected cells takes place at the endoplasmic reticulum (ER). The viral structural glycoproteins prM and E localize to the luminal side of the ER and form an immature particle with prM and E in a heterodimeric complex. Proteolysis of prM in the trans-Golgi network triggers rearrangement, homodimerization of E, and formation of the mature viral particle before release from the infected cell. During normal virus assembly in mammalian cells a 14-residue oligosaccharide, (Glc)3(Man)9(GlcNAc)2, is added in the ER to specific asparagine residues on the prM and E proteins. This high-mannose carbohydrate is normally sequentially modified in the ER by resident α-glucosidases to generate N-linked glycans that lack the terminal α1,2- and both α1,3-glucose residues which are then normally converted to complex-type oligosaccharide moieties. This processing of N-linked carbohydrates in the ER is required for proper assembly and secretion of the Dengue virus (Courageot, M-P, Frenkiel, M-P, et al. (2000) *J Virol*, 74, 564-572; Wu, S. F., C. J. Lee, C. L. Liao et al. (2002) *J Virol.*, 76, 3596-3604). It is believed that the effect of castanospermine on normal glycoprotein processing inhibits secretion and infectivity of Dengue viral particles. These antiviral properties may have utility in treating Dengue virus infections in humans (Whitby, K., Pierson, T. C., Geiss, B., et al. (2005) *J Virol*, 79, 8698-8706).

Other viruses that are genetically related to Dengue virus are known to cause yellow fever, hepatitis C, and the Japanese, St. Louis, and West Nile encephalitis. Studies of Japanese encephalitis virus with a different α-glucosidase inhibitor, N-nonyl-deoxynojirimycin (NN-DNJ), suppressed cell infection but to a lesser extent than with Dengue virus (Wu, S. F., C. J. Lee, C. L. Liao et al. (2002) *J. Virol.*, 76, 3596-3604). In these experiments, there was a decreased mortality rate among mice given a lethal dose of Japanese encephalitis virus upon treatment with NN-DNJ. Thus, at least some flaviviruses appear sensitive to alpha-glucosidase inhibitors, such as castanospermine and deoxynojirimycin (Whitby, K., Pierson, T. C., Geiss, B., et al. (2005) *J Virol*, 79, 8698-8706). West Nile Virus is one Flavivirus that is insensitive to castanospermine. Other studies have documented that alpha-glucosidase inhibitors reduce infection of some RNA and DNA viruses (McGinnes, L. W., and T. G. Morrison (1998) *Virus Res*, 53, 175-185).

The Zika virus is a Flavivirus that is spread to humans through mosquito bites. It is presently a major human health concern. Although Zika virus infection often causes no or only mild symptoms, Zika virus may spread from a pregnant women to the baby resulting in microcephaly and other severe brain problems. Further, the World Health Organization (WHO) indicates there is strong scientific consensus that Zika virus infections in adults can result in Guillain-Barré syndrome, a neurological syndrome that can cause temporary paralysis. Zika virus prevalence is highest within a narrow equatorial belt from Africa to Asia. In the United States, Zika virus is found in Florida and portions of other states bordering on the Gulf of Mexico. Overall, there are over 2 billion people that live in regions of the world impacted by the Zika virus. There are presently no vaccines or medications capable of preventing or treating Zika virus infections.

BRIEF SUMMARY OF THE INVENTION

The present invention concerns the use of alpha-glucosidase inhibitors for the treatment or prevention of Zika virus infections. In some embodiments, the alpha-glucosidase inhibitor comprises an alpha-glucosidase I inhibitor (sometimes referred to as a glucosidase I inhibitor), such as castanospermine or deoxynojirimycin.

One aspect of the invention is a method for treatment or prevention of Zika virus infection, comprising administering an alpha-glucosidase inhibitor to a human or non-human animal subject in need thereof. In some embodiments, the alpha-glucosidase inhibitor is administered to a subject infected by Zika virus, as therapy. In other embodiments, the alpha-glucosidase inhibitor is administered to a subject not infected by Zika virus, as prophylaxis (to prevent or delay the onset of Zika infection).

In some embodiments of the method, the alpha-glucosidase inhibitor comprises castanospermine, acarbose, miglitol voglibose, emiglitate, kotalanol, or a derivative of any of the foregoing that retains alpha-glucosidase inhibitory activity. In some embodiments, the alpha-glucosidase inhibitor comprises castanospermine, or a derivative or prodrug of castanospermine.

Another aspect of the invention concerns a composition comprising an alpha-glucosidase inhibitor for treatment of Zika virus infections. In some embodiments of the composition, the alpha-glucosidase inhibitor comprises castanospermine, acarbose, miglitol voglibose, emiglitate, kotalanol, or a derivative or prodrug of any of the foregoing that retains alpha-glucosidase inhibitory activity. In some embodiments, the alpha-glucosidase inhibitor comprises castanospermine. In some embodiments, the composition comprises a packaged dosage formulation or a kit for treatment or prevention of a Zika virus infection.

BRIEF DESCRIPTION OF THE DRAWINGS

FIG. 1. Castanospermine as anti-ZIKV compound. Castanospermine was screened for antiviral activity against ZIKV infection. Glioblastoma SNB-19 cells were treated with castanospermine at the indicated concentrations one hour prior to inoculation with the FSS-13025 strain of ZIKV (at MOI=1). Cells were harvested 24 hours post-infection and analyzed by Western blot for ZIKV-NS1 or GAPDH.

DETAILED DESCRIPTION OF THE INVENTION

Figures 2A, 2B:
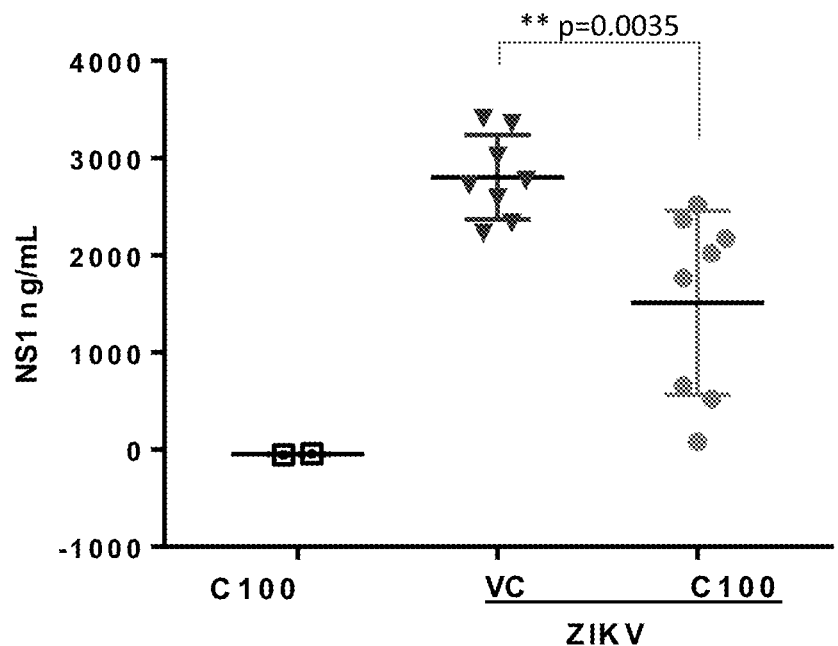
FIGS. 2A-2B. Zika viral load in serum in Ifnar 1−/− mice. Serum was separated from the blood by centrifugation. Viral load (NS1) was estimated using the ZIKV NS1 ELISA Kit (BioFront Technologies, Fl, USA) as per the manual. Statistical analysis was done by unpaired t-test using GraphPad Prism software. *$p<0.05$ is considered as significant (FIG. 2B). With castanospermine treatment, there was 46% reduction in Zika virus load as estimated by NS1 protein in the serum (FIG. 2A).

An aspect of the invention concerns a method for treatment of Zika virus infection comprising administering an effective amount of an alpha-glucosidase inhibitor to a human or non-human animal subject infected by Zika virus, thereby treating the Zika virus infection.

In some embodiments of the methods, the alpha-glucosidase inhibitor comprises castanospermine, acarbose, miglitol voglibose, emiglitate, or a derivative or prodrug of any of the foregoing that retains alpha-glucosidase inhibitory activity. In some embodiments of the methods, the alpha-glucosidase inhibitor comprises castanospermine, or a derivative or prodrug of castanospermine, such as the prodrug celgosivir (6-O-butanoyl castanospermine).

Another aspect of the invention concerns a method for inhibiting a Zika virus infection in a cell comprising contacting the cell in vitro or in vivo with an alpha-glucosidase inhibitor before or after the cell is infected.

Another aspect of the invention concerns a composition comprising an α-glucosidase inhibitor. In some embodiments of the compositions, the α-glucosidase inhibitor comprises castanospermine, acarbose, miglitol voglibose, emiglitate, or a derivative or prodrug of any of the foregoing that retains α-glucosidase inhibitory activity.

In some embodiments of the compositions, the α-glucosidase inhibitor comprises castanospermine, or a derivative or prodrug of castanospermine that retains α-glucosidase inhibitory activity, or a derivative or prodrug of castanospermine such as celgosivir.

Alpha-Glucosidase Inhibitors

Alpha-glucosidase hydrolyzes terminal non-reducing 1-4 linked alpha-glucose residues to release a single alpha-glucose molecule. Alpha-glucosidase is a carbohydrate-hydrolase that releases alpha-glucose as opposed to beta-glucose. Alpha-glucosidases include maltase, glucoinvertase, glucosidosucrase, maltase-glucoamylase, alpha-glucopyranosidase, glucosidoinvertase, alpha-D-glucosidase, alpha-glucoside hydrolase, alpha-1,4-glucosidase, and alpha-D-glucoside glucohydrolase.

Alpha-glucosidase inhibitors include inhibitors of alpha-glucosidase production, inhibitors of glycoprotein processing, and inhibitors of alpha-glucosidase activity. Glycoprotein processing inhibitors interfere with the normal processing of N-linked glycoproteins by inhibiting glycosidases involved in these reactions. Compounds that inhibit alpha-glucosidase I and II prevent the removal of glucoses from high-mannose chains (see, for example, Kaushal G P et al., "Selective inhibition of glycoprotein processing enzymes. Differential inhibition of glucosidases I and II in cell culture," *J Biol Chem.*, 1988, 263(33):17278-17283; Albein A D, "Glycosidase inhibitors as antiviral and/or antitumor agents," *Semin Cell Biol.*, 1991, 2(5):309-317; and Albein A D, "Glycosidase inhibitors: inhibitors of N-linked oligosaccharide processing," *FASEB J*, 1991, 5(15):3055-3063; Jacob G S, "Glycosylation inhibitors in biology and medicine", *Curr Opin Struct Biol.*, 1995, 5(5): 605-611; and Kajimoto T and Node M, "Inhibitors against glycosidases as medicines," *Curr Top Med Chem*, 2009, 9(1):13-33, each of which are incorporated by reference herein in their entirety).

Several alpha-glucosidases function in breaking down polysaccharides of glucose such as starch or glycogen. Because of this, inhibitors of these enzymes often have utility in the treatment of diabetes. Typically, the alpha-glucosidase inhibitors to be used in the various aspects of the invention (e.g., methods, compositions, packaged dosage formulations, and kits) are inhibitors of alpha-glucosidase I (also referred to as "glucosidase I"). This enzyme catalyzes the first steps in glycoprotein processing, wherein a (Glc)3 (Man)9(GlcNAc)2 structure is transferred enblock onto an Asn residue of a glycoprotein. Once attached, the first operation is to remove the Glc3 residues (later processing takes off many of the Man residues). As alpha-glucosidase I inhibitors, compounds such as castanospermine and deoxynojirimycin inhibit this reaction. Although the alpha-glucosidase inhibitors used in the various aspects of the invention may inhibit other glucosidase enzymes (in addition to alpha-glucosidase I), the inhibitors used will typically inhibit at least alpha-glucosidase I. In some embodiments, the alpha-glucosidase inhibitor used only inhibits alpha-glucosidase I. In some embodiments, the alpha-glucosidase inhibitor used inhibits alpha-glucosidase I and II.

Alpha-glucosidase inhibitors can inhibit the degradation and digestion of carbohydrate and thus limit an abrupt increase in postprandial blood glucose levels. The alpha-glucosidase inhibitors used in the various aspects of the invention may be any type of substance, such as a small molecule, polypeptide, nucleic acid, or extract. For example, a methanolic extract of *Centaurea calcitrapa* (Red start thistle) has been identified as having alpha-glucosidase activity (Kaskoos R (2013), *American Journal of Essential Oils and Natural Products*, vol. 1, no. 1, pp. 122-125). In some embodiments, the alpha-glucosidase inhibitor is one that acts as a competitive inhibitor of alpha-glucosidase.

In some embodiments, the alpha-glucosidase inhibitor is a saccharide that acts as competitive inhibitor of alpha-glucosidase. Nucleic acids that act as alpha-glucosidase inhibitors may act to inhibit the alpha-glucosidase, for example, by targeting and directly or indirectly interacting with the DNA or mRNA encoding alpha-glucosidase and therefore reducing alpha-glucosidase expression, or the nucleic acids may act through a polypeptide that is encoded by the nucleic acid molecule.

In some embodiments, the alpha-glucosidase inhibitor is an inhibitor of intestinal alpha-glucosidase of the intended subject. In some embodiments, the alpha-glucosidase inhibitor is an inhibitor of lysosomal alpha-glucosidase of the intended subject.

Inhibitors of alpha-glucosidase production include antisense molecules (e.g., antisense oligodeoxynucleotides (ODNs)) or small interfering RNA (siRNA) against the mRNA transcript for the alpha-glucosidase. Agents which decrease alpha-glucosidase bioavailability include neutralizing antibodies against alpha-glucosidase, soluble receptors or other proteins which can be engineered to bind alpha-glucosidase with higher affinity than its substrate in target tissues. Inhibitors of the alpha-glucosidase include neutralizing antibodies, inhibitory peptides or small molecule inhibitors which prevent alpha-glucosidase from binding to its substrate and/or otherwise carrying out its enzymatic activity in target tissues. In some embodiments, the alpha-glucosidase inhibitor comprises an antisense molecule, ribozyme, siRNA, or triplex forming nucleic acid.

Methods of measuring amounts of nucleic acids (e.g., RT-PCR) and protein (e.g., ELISA), and for screening for alpha-glucosidase enzyme activity, are known and can be used to identify agents that have alpha-glucosidase inhibitory activity (see Y.-M. Kim (2003), *Nutrition*, vol. 21, no. 6, pp. 756-761, and alpha-glucosidase assay kit (catalog no. KA 1608, Abnova; and catalog no. ab174093, Abcam)). Homology modeling of human alpha-glucosidase catalytic domains has been conducted and structure-activity-relationships have been studied (see, for example, Nakamura S. et al. (2012), *Open Journal of Medicinal Chemistry*, Vol. 2, pp. 50-60, which is incorporated herein by reference in its entirety).

In some embodiments, the alpha-glucosidase inhibitor comprises a pseudoglucosylamine, such as validamine, valienamine, valiolamine, N-substituted valiolamine derivative, acarviosin derivative, acarbose, or higher pseudo-oligosaccharide.

In some embodiments, the alpha-glucosidase inhibitor comprises a polyhydroxypiperidine or polyhydroxypyrrolidine, such as nojirimycin, 1-deoxynojirimycin, N-substituted derivative of 1-deoxynojirimycin, branched and/or chain-extended deoxynojirimycin (DNJ) derivatives (e.g., derivatives branched at C-1, branched at C-5, chain-extended at C-6), deoxy, amino, or halogen derivative, polyhydroxypiperidine with an altered configuration, bicyclic derivative of deoxynojirimycin (e.g., castanospermine or castanospermine derivatives), or polyhydroxypyrrolidine (e.g., monocyclic pyrrolidine derivative or bicyclic pyrrolidine derivative). In some embodiments, the alpha-glucosidase inhibitor is a higher N-alkyl derivative of DNJ, having an increased alkyl chain length of at least 5 carbon atoms to about 10 carbon atoms, relative to lower $C_1$-$C_4$ N-alkyl derivatives.

In some embodiments, the alpha-glucosidase inhibitor comprises a sulfonium ion (see, for example, Mohana S et al. (2012), *International Journal of Antimicrobial Agents*, vol. 40, no. 3, pp. 273-276, incorporated herein by reference in its entirety). In some embodiments, the alpha-glucosidase inhibitor comprises an imino sugar (e.g., DNJ, or a DNJ derivative with alkylation of the ring nitrogen (see, for example, Sayce A C et al. (2016), *PLOS Neglected Tropical Diseases*, vol. 10, issue 3, pp. 1-22; and Chang J et al. (2013), *Emerging Microbes and Infections*, e77); Chang J et al. (2011), *Antiviral Res.*, vol. 92, no. 2, pp. 369-371, which are each incorporated herein by reference in their entirety). Imino sugars are glucose mimetics with a nitrogen atom in place of a ring oxygen and are competitive inhibitors of ER-resident alpha-glucosidases I and II.

In some embodiments, the alpha-glucosidase inhibitor comprises castanospermine (CAS No. 79831-76-8; a.k.a. (1S,6S,7R,8aR)-Tetrahydroxyoctahydroindolizine), acarbose (CAS No. 56180-94-0; a.k.a. 4",6"-Dideoxy-4"-([1S]-[1,4,6/5]-4,5,6-trihydroxy-3-hydroxymethyl-2-yclohexenylamino)-maltotriose), miglitol (CAS No. 72432-03-2; a.k.a. (2R,3R,4R,5 S)-1-(2-Hydroxyethyl)-2-(2-hydroxymethyl)-3,4,5-piperidinetriol), voglibose (CAS No. 83480-29-9; a.k.a. 3,4-Dideoxy-4-[[2-hydroxy-1-(hydroxymethyl)ethyl]amino]-2-C-(hydroxymethyl)-D-epi-inositol), emiglitate (CAS No. 80879-63-6; a.k.a. ethyl 4-[2-[(2R,3R,4R,5 S)-3,4,5-trihydroxy-2-(hydroxymethyl)piperidin-1-yl]ethoxy]benzoate), kotalanol (CAS No. 214491-0-73; a.k.a. 1,4-Dideoxy-1,4-[(S)-[7-deoxy-5-O-sulfo-D-glycero-D-galacto-heptitol-7-yl]episulfoniumylidene]-D-arabinitol inner salt), salacinol (CAS No. 200399-47-9; a.k.a. 1,4-Dideoxy-1,4-[(S)-[(2S,3S)-2,4-dihydroxy-3-(sulfooxy)butyl] epi sulfoniumylidene]-D-arabinitol inner salt); N-nonyl-deoxynojirimycin (NN-DNJ; CAS No. 81117-35-3) or a derivative of any of the foregoing that retains α-glucosidase inhibitory activity.

Other alpha-glucosidase inhibitors that may be utilized include those disclosed in U.S. Pat. Nos. 4,065,562; 4,182,767; 4,278,683; 4,533,668; and 4,639,436; Mohana S et al. (2012), *International Journal of Antimicrobial Agents*, vol. 40, no. 3, pp. 273-276; Courageot M-P et al. (2000), *Journal of Virology*, vol. 74, no. 1, pp. 564-572; Warfield K L et al. (2016), *Antiviral Research*, vol. 129 pp. 93-98; Sayce A C et al. (2016), *PLOS Neglected Tropical Diseases*, vol. 10, issue 3, pp. 1-22; Krishnan M N and MA Garcia-Blanco, *Viruses* (2014), vol. 6, pp. 683-708); Lu Y et al. (2014), *Molecules*, vol. 19, pp. 8544-8555, which are each incorporated reference in their entireties). Some general features of some representative classes of alpha-glucosidase inhibitors are shown and described in Gloster T M and GJ Davies, *Org. Biomol. Chem.*, 2010, vol. 8, pp. 305-320, particularly FIG. 3, which is incorporated herein by reference in its entirety (FIG. 3 and the entire document).

Derivatives, Prodrugs, and Stereoisomers of Alpha-Glucosidase Inhibitors

Derivatives of parent molecules that retain alpha-glucosidase inhibitory activity (the same activity, or different alpha-glucosidase activity in type or extent) are known and can be utilized (see, for example, Chapter 15, pp. 411-467, "Chemistry and Structure-Activity Relationships of Glucosidase Inhibitors", Jung B et al., in *Oral Antidiabetics*, Eds. Jochen Kuhlmann and Walter Puls, Springer-Verlag Berlin Heidelberg, 1996, which is incorporated herein by reference in its entirety). Analytical methods for detecting and identifying glucosidase inhibitors are known (see, for example, Chapter 16, pp. 483-494, "Analytical Methods of Determination of Glucosidase Inhibitors", Ploschke H J et al., in *Oral Antidiabetics*, 1996, which is incorporated herein by reference in its entirety). The pharmacology and metabolism of glucosidase inhibitors has been studied (see, for example, Chapter 17, pp. 497-525, "Pharmacology of Glucosidase Inhibitors", Puls W; and Chapter 18, pp. 535-538, "General Pharmacology of Glucosidase Inhibitors, Puls W; Chapter 19, pp. 541-554, "Pharmacokinetics and Metabolism of Glucosidase Inhibitors", Krause H P and HJ Ahr; and Chapter 21, pp. 611-628, "Clinical Pharmacology of Glucosidase Inhibitors," Brendel E and W Wingender, in *Oral Antidiabetics*, 1996, which are each incorporated herein by reference in their entirety).

Derivatives of the alpha-glucosidase inhibitors exemplified herein can be synthesized by chemical transformations of the compounds' functional groups using standard chemical reactions. For example, these standard chemical reactions can include, but are not limited to: polar reactions under basic conditions, polar reactions under acidic conditions, pericyclic reactions, and free radical reactions. In another example, these standard chemical reactions can include, but are not limited to: addition reactions, substitution reactions, oxidation reactions, reduction reactions, elimination reactions, hydrolysis, acylation, amidations, etherification, and esterification. Alkane functional group transformations can include, but are not limited to: free radical chlorination (hv, $Cl_2$), free radical bromination (hv, $Br_2$), and allylic bromination (NBS). Alkene functional group transformations can include, but are not limited to: addition of HCl, addition of HBr, addition of HI, addition of $H_3O(+)$, chlorination ($Cl_2$) bromination ($Br_2$), iodination ($I_2$), chlorohydrin formation ($Cl_2/H_2O$), bromohydrin formation ($Br_2/H_2O$), ether formation (H+/ROH), oxymercuration ($Hg(OAc)_2/H_2O$), oxymercuration, ($Hg(OAc)_2/$ROH), hydroboration, epoxidation ($RCO_3H$), dihydroxylation ($OsO_4$), dihydroxylation ($KMnO_4$), cyclopropanation, dichlorocyclopropanation, ozonolysis (reductive workup), ozonolysis (oxidative workup), oxidative cleavage ($KMnO_4$), hydrogenation, rearrangements (H shift), rearrangements (alkyl shift), free radical addition of HBr, and Sharpless epoxidation. Alkyne functional group transformations can include, but are not limited to: deprotonation (acetylide formation), $S_N2$ with alkyl halides, partial reduction (Lindlar), partial, reduction ($Na/NH_3$), hydroboration, oxymercuration, addition of HCl, HBr, or HI, addition of HCl, HBr, or HI, hydrogenation, ozonolysis, oxidative cleavage ($KMnO_4$), and halogenation ($Cl_2$, $Br_2$, $I_2$). The substitution reaction can include, but is not limited to: alcohol formation, nitrile formation, thiol formation, ether formation, thioether formation, azides, ester formation, acetylide addition, alkanes (Gilman reagents), ammonium salt formation, alkyl chloride formation, alkyl bromide formation, alkyl iodide formation, alkyl shift, and hydride shift. Elimination reactions can include, but are not limited to: alkenes from alkyl halides, alkenes from alcohols (strong acid), alkenes from alcohols ($POCl_3$), alkenes from alkyl halides, E1 with rearrangement (alkyl shift), Hoffmann elimination, and alkyne formation via elimination E1 with rearrangement (hydride shift). Organometallic reactions can include, but are not limited to: Grignard formation (alkyl halides), Grignard formation (alkenyl halides), reaction of Grignards with acids, addition of Grignards to aldehydes, addition of Grignards to ketones, addition of Grignards to esters, reaction of Grignards with $CO_2$, addition of Grignards to nitriles, formation of organolithium reagents, formation of Gilman reagents, $S_N2$ with Gilman reagents, addition of Gilman reagents to enones, addition of Gilman to acyl halides, Heck reaction, Suzuki reaction, and Stille reaction. Reactions of epoxides can include, but are not limited to: epoxide opening (basic conditions), epoxide opening (acidic conditions), epoxide opening (diol formation), epoxide formation (from halohydrins), epoxide formation (from alkenes), and Sharpless epoxidation of alkenes. Reactions of alcohols and thiols can include, but are not limited to: deprotonation (alkoxide formation), protonation (onium ion formation), conversion to tosylates/mesylates, conversion to alkyl chlorides ($SOCl_2$), conversion to alkyl bromides ($PBr_3$), oxidation to aldehydes (PCC), oxidation to ketones (PCC+others), oxidation to carboxylic acid, ($H_2CrO_4$+others), protection as silyl ethers, thiol formation ($S_N2$), and thiol oxidation to disulfides. Reactions of dienes can include, but are not limited to: Diels-alder reaction, polymerization of dienes, reactions of aromatics (arenes), nitration ($HNO_3/H_2SO_4$), chlorination ($Cl_2$ plus catalyst), bromination ($Br_2$ plus catalyst), sulfonylation ($SO_3/H_2SO_4$), Friedel Crafts alkylation (R-X plus catalyst), Friedel Crafts acylation (RCOX plus catalyst), iodination ($I_2$/catalyst), Side chain oxidation ($KMnO_4$), reduction of nitro groups, reduction of aromatic ketones, Side chain bromination, nucleophilic aromatic substitution ($S_NAr$), and aryne formation ($S_NAr$ via arynes). Reactions of aldehydes and ketones can include, but are not limited to: hydrate formation ($H_2O$), cyanohydrin formation (CN), reduction of aldehydes ($NaBH_4$), reduction of aldehydes ($LiAlH_4$), reduction of ketones ($NaBH_4$), reduction of ketones ($LiAlH_4$), Grignard addition to aldehydes, Grignard addition to ketones, acetal formation (ROH/H+), acetal hydrolysis ($H_3O^+$), imine, formation ($RNH_2$), Enamine formation ($R_2NH$), Wolff-Kishner: reduction to alkanes, Clemmensen, reduction to alkanes, oxidation to carboxylic acid ($H_2CrO_4$ or $KMnO_4$), keto-enol tautomerism, enolate formation, aldol addition reaction, alkylation of enolates, Wittig reaction (alkene formation), thioacetal formation, imine hydrolysis, oxidation to carboxylic acids (Tollens), haloform reaction, Baeyer-Villiger reaction, aldol condensation, Cannizarro reaction. Reactions of carboxylic acids can include, but are not limited to: deprotonation (carboxylate formation), formation via Grignard and $CO_2$, conversion to acid chloride ($SOCl_2$), reduction ($LiAlH_4$), Fischer esterification, and decarboxylation (of β-keto acids). Reactions of esters can include, but are not limited to: reduction to aldehydes (DIBAL-H), reduction to alcohols ($LiAlH_4$), hydrolysis to carboxylic acid (acidic), hydrolysis to carboxylic acid (basic), addition of Grignard reagents to esters, Claisen condensation, and transesterification (basic conditions). Reactions of acyl halides can include, but are not limited to: conversion to esters (ROH), conversion to carboxylic acids ($H_2O$), conversion to anhydrides ($RCO_2$), conversion to amides ($RNH_2$), conversion to ketones (Gilman reagents), and conversion to aldehydes ($LiAlH(OtBu)_3$). Reactions of α,β-unsaturated ketones (enones) can include, but are not limited to: Michael reaction (conjugate addition of enolates), conjugate addition of Gilman reagents, conjugate addition of other nucleophiles. Reactions of amines and amides can include, but are not limited to: dehydration of amides to nitriles (P$_2$O$_5$), Hofmann rearrangement, Gabriel synthesis of amines, reductive amination, formation of diazonium salts, reactions of diazonium salts, amide formation using DCC, amide formation from acid halides, and Curtius rearrangement. Reactions of nitriles can include, but are not limited to: addition of Grignard reagents to nitriles, reduction to amines (LiAlH$_4$), hydrolysis to carboxylic acids. Optionally, potential derivatives of alpha-glucosidase inhibitors exemplified herein, such as derivatives of castanospermine, can be tested for glycoprotein processing inhibition and/or anti-Zika virus activity using methods disclosed herein (e.g., in the Examples) or using other methods known in the art.

By way of example only, castanospermine derivatives have been known for some time (Kang M S et al., "Castanospermine analogues: their inhibition of glycoprotein processing α-glucosidases from porcine kidney and B 16F10 cells," *Glycobiolog*; (1995) 5 (1): 147-152; Winchester B G et al., "The structural basis of the inhibition of human glycosidases by castanospermine analogues," *Biochem. J.* (1990) 269, 227-231; Aguilar-Moncayo M et al., Glycosidase inhibition by ring-modified castanospermine analogues: tackling enzyme selectivity by inhibitor tailoring, *Org. Biomol. Chem.* (1999) 7:2738-47; Tyler P C and BG Winchester, Chapter 7, "Synthesis and Biological Activity of Castanospermine and Close Analogs", in Iminosugars as Glycosidase Inhibitors: Nojirimycin and Beyond, (ed A. E. Stütz), Wiley-VCH Verlag GmbH & Co. KGaA, Weinheim, FRG; U.S. Pat. No. 5,004,476 (Liu P S et al., "Anti-retroviral castanospermine esters"); and U.S. Pat. No. 5,017,563 (Liu P S et al., "Castanospermine esters and glycosides"), which are each incorporated herein by reference in their entirety.

FIG. 4 shows a chemical structure illustrating an embodiment of alpha-glucosidase I inhibitors (also referred to as glucosidase I inhibitors), where $R_1$, $R_2$, $R_3$, $R_4$, and $R_5$, can be independently selected from the group consisting of: a H; F; Cl; Br; I; OH; CN; $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; alkynyl; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; thiol; thioalkyl; alkoxy; alkylthio; alkoxyalkyl; aryloxy; arylalkoxy; acyloxy; nitro; carbamoyl; trifluoromethyl; phenoxy; benzyloxy; phosphonic acid; phosphate ester; sulfonic acid ($—SO_3H$); sulfonate ester; sulfonamide; alkaryl; arylalkyl; carbamate; amino; alkylamino; arylamino; dialkylamino; alkylarylamino; diarylamino; alkylthio; heteroalkyl; alkyltriphenylphosphonium; heterocyclyl; ketone (═O); ether ($—OR_6$); and ester ($—COOR_7$ and $—OC(═O)R_7$);

where $R_6$ can be independently selected from the group consisting of: a $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; and alkynyl; and where $R_7$ can be independently selected from the group consisting of: a $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; and alkynyl.

The structure of FIG. 4 encompasses castanospermine and some derivatives of castanospermine. In one embodiment, the derivative of castanospermine in FIG. 4 is celgosivir (where R1 would be ester ($—OC(═O)R_7$) with R7 as n-propyl; R2, R3, and R5 would be OH; and R4 would be H).

FIG. 5 shows a chemical structure illustrating an embodiment of alpha-glucosidase I inhibitors (also referred to as glucosidase I inhibitors), where $R_1$, $R_2$, $R_3$, $R_4$, and $R_5$, can be independently selected from the group consisting of: a H; F; Cl; Br; I; OH; CN; $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; alkynyl; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; thiol; thioalkyl; alkoxy; alkylthio; alkoxyalkyl; aryloxy; arylalkoxy; acyloxy; nitro; carbamoyl; trifluoromethyl; phenoxy; benzyloxy; phosphonic acid; phosphate ester; sulfonic acid ($—SO_3H$); sulfonate ester; sulfonamide; alkaryl; arylalkyl; carbamate; amino; alkylamino; arylamino; dialkylamino; alkylarylamino; diarylamino; alkylthio; heteroalkyl; alkyltriphenylphosphonium; heterocyclyl; ketone (═O); ether ($—OR_6$); and ester ($—COOR_7$ and $—OC(═O)R_7$);

where $R_6$ can be independently selected from the group consisting of: a $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; and alkynyl; and where $R_7$ can be independently selected from the group consisting of: a $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; and alkynyl.

The structure of FIG. 5 encompasses nojirimycin and some derivatives of nojirimycin. In one embodiment, the derivative of nojirimycin in FIG. 5 is 1-Deoxynojirimycin (DNJ) (where R1, R2, R3, and R4 are OH, and R5 is H).

Depending upon their molecular structure, the alpha-glucosidase inhibitors can be chiral and can accordingly occur in various enantiomeric forms. They can therefore exist in racemic or in optically active form.

Since the pharmaceutical activity of the racemates or stereoisomers of the alpha-glucosidase inhibitors may differ, it may be desirable to use the enantiomers. In these cases, the end product or even the intermediates can be separated into enantiomeric compounds by chemical or physical measures known to the person skilled in the art or even employed as such in the synthesis.

Any reference herein to a specific compound (e.g., castanospermine) should be understood as a reference to any enantiomer or mixture thereof. Any enantiomer may be substantially free of others, e.g., in an enantiomeric excess of at least 80%, preferably at least 90% and more preferably at least 95%. Similarly, any mixture of diastereomers may be substantially free of the other.

By way of example only, methods for synthesis of castanospermine enantiomers are known in the art (see, for example, Tiwari D K et al., "Divergent total synthesis of 1,6,8a-tri-epi-castanospermine and 1-deoxy-6,8a-di-epi-castanospermine from substituted azetidin-2-one (β-lactam), involving a cascade sequence of reactions as a key step", Org Biomol Chem. (2014) 12(37):7389-7396; Cesson J et al., "Asymmetric synthesis of (+)-castanospermine through enol ether metathesis-hydroboration/oxidation", Organic & Biological Chemistry, 2009, Issue 10; RC Bernotas and B. Ganem, "Total syntheses of (+)-castanospermine and (+)deoxynojirimycin," Tetrahedron Lett (1984) 25:165-168; Burgess K, "Synthetic approaches to stereoisomers and analogues of castanospermine," Tetrahedron, 48(20):4045-4066; and Burgess K et al., "A route to several stereoisomers of castanspermine, Journal of Organic Chemistry (1992), 57(4):1103-1109, each of which are incorporated herein by reference in their entirety).

Nucleic Acid and Polypeptide Inhibitors of Alpha-Glucosidase

Nucleic acids useful in the invention include sequences encoding any protein that decreases synthesis or amounts of alpha-glucosidase, or that directly or indirectly contributes to a lack of alpha-glucosidase production or accumulation. Such sequences therefore include inhibitory nucleic acids such as antisense molecules and interfering RNA (e.g., siRNA, shRNA).

Additional nucleic acid sequences useful in the invention include sequences encoding proteins that directly or indirectly modulate expression or activity of any protein that participates in alpha-glucosidase accumulation. Particular examples include proteins that reduce expression or activity of alpha-glucosidase enzyme. Such sequences therefore include proteins that regulate transcription or translation of alpha-glucosidase enzyme. Accordingly, nucleic acids encoding such proteins or targeting such proteins for inhibition can also be used in accordance with the invention.

The terms "nucleic acid," "polynucleotide" refers to at least two or more ribo- or deoxy-ribonucleic acid base pairs (nucleotides) that are linked through a phosphoester bond or equivalent. Nucleic acids include polynucleotides and polynucleosides. Nucleic acids include single, double or triplex, circular or linear, molecules. A nucleic acid molecule may belong exclusively or in a mixture to any group of nucleotide-containing molecules, as exemplified by, but not limited to: RNA, DNA, cDNA, genomic nucleic acid, non-genomic nucleic acid, naturally occurring and non-naturally occurring nucleic acid and synthetic nucleic acid.

Nucleic acids can be of any length. Nucleic acid lengths useful in the invention typically range from about 20 nucleotides to 20 Kb, 10 nucleotides to 10 Kb, 1 to 5 Kb or less, 1000 to about 500 nucleotides or less in length. Nucleic acids can also be shorter, for example, 100 to about 500 nucleotides, or from about 12 to 25, 25 to 50, 50 to 100, 100 to 250, or about 250 to 500 nucleotides in length. Shorter polynucleotides are commonly referred to as "oligonucleotides" or "probes" of single- or double-stranded DNA. However, there is no upper limit to the length of such oligonucleotides.

Polynucleotides include L- or D-forms and mixtures thereof, which additionally may be modified to be resistant to degradation when administered to a subject. Particular examples include 5' and 3' linkages that are resistant to endonucleases and exonucleases present in various tissues or fluids of a subject.

Nucleic acids include antisense. As used herein, the term "antisense" refers to a polynucleotide or peptide nucleic acid capable of binding to a specific DNA or RNA sequence. Antisense includes single, double, triple or greater stranded RNA and DNA polynucleotides and peptide nucleic acids (PNAs) that bind RNA transcript or DNA. Particular examples include RNA and DNA antisense that binds to sense RNA. For example, a single stranded nucleic acid can target an alpha-glucosidase transcript (e.g., mRNA). Antisense molecules are typically 100% complementary to the sense strand but can be "partially" complementary, in which only some of the nucleotides bind to the sense molecule (less than 100% complementary, e.g., 95%, 90%, 80%, 70% and sometimes less).

Triplex forming antisense can bind to double strand DNA thereby inhibiting transcription of the gene. Oligonucleotides derived from the transcription initiation site of the gene, e.g., between positions −10 and +10 from the start site, are a particular example.

Short interfering RNA (referred to as siRNA or RNAi) for inhibiting gene expression is known in the art (see, e.g., Kennerdell et al., Cell 95:1017 (1998); Fire et al., Nature, 391:806 (1998); WO 02/44321; WO 01/68836; WO 00/44895, WO 99/32619, WO 01/75164, WO 01/92513, WO 01/29058, WO 01/89304, WO 02/16620; and WO 02/29858). RNAi silencing can be induced by a nucleic acid encoding an RNA that forms a "hairpin" structure or by expressing RNA from each end of an encoding nucleic acid, making two RNA molecules that hybridize.

Ribozymes, which are enzymatic RNA molecules that catalyze the specific cleavage of RNA can be used to inhibit expression of the encoded protein. Ribozymes form sequence-specific hybrids with complementary target RNA, which is then cleaved. Specific examples include engineered hammerhead motif ribozyme molecules that can specifically and efficiently catalyze endonucleolytic cleavage of sequences encoding an alpha-glucosidase enzyme.

Ribozyme cleavage sites within a potential RNA target can be initially identified by scanning the target molecule for cleavage sites which include, for example, GUA, GUU, and GUC. Once identified, RNA sequences of between about 15 and 20 ribonucleotides corresponding to the region of the target containing the cleavage site are evaluated for secondary structural features which may render the oligonucleotide inoperable. The suitability of candidate target sequences may also be evaluated by testing accessibility to hybridization with complementary oligonucleotides using ribonuclease protection assays.

Antisense, ribozymes, RNAi and triplex forming nucleic acid are referred to collectively herein as "inhibitory nucleic acid" or "inhibitory polynucleotides." Such inhibitory nucleic acids can inhibit expression of an alpha-glucosidase enzyme.

Inhibitory polynucleotides do not require expression control elements to function in vivo. Such molecules can be absorbed by the cell or enter the cell via passive diffusion. Such molecules may also be introduced into a cell using a vector, such as a viral vector. Inhibitory polynucleotides may be encoded by a nucleic acid so that it is transcribed. Furthermore, such a nucleic acid encoding an inhibitory polynucleotide may be operatively linked to an expression control element for sustained or increased expression of the encoded antisense in cells or in vivo.

Inhibitory nucleic acid can be designed based on gene sequences available in the publicly available databases. For example, Genbank sequences for exemplary alpha-glucosidase enzymes are known in the art and can be used to design inhibitory nucleic acids.

Nucleic acids further include nucleotide and nucleoside substitutions, additions and deletions, as well as derivatized forms and fusion/chimeric sequences (e.g., encoding recombinant polypeptide). For example, due to the degeneracy of the genetic code, nucleic acids include sequences and subsequences degenerate with respect to nucleic acids that encode amino acid sequences of alpha-glucosidase. Other examples are nucleic acids complementary to a sequence that encodes an amino acid sequence of an alpha-glucosidase enzyme.

Nucleic acid deletions (subsequences and fragments) can have from about 10 to 25, 25 to 50 or 50 to 100 nucleotides. Such nucleic acids are useful for expressing polypeptide subsequences, for genetic manipulation (as primers and templates for PCR amplification), and as probes to detect the presence or an amount of a sequence encoding a protein (e.g., via hybridization), in a cell, culture medium, biological sample (e.g., tissue, organ, blood or serum), or in a subject.

The term "hybridize" and grammatical variations thereof refers to the binding between nucleic acid sequences. Hybridizing sequences will generally have more than about 50% homology to a nucleic acid that encodes an amino acid sequence of a reference sequence. The hybridization region between hybridizing sequences can extend over at least about 10-15 nucleotides, 15-20 nucleotides, 20-30 nucleotides, 30-50 nucleotides, 50-100 nucleotides, or about 100 to 200 nucleotides or more.

Nucleic acids can be produced using various standard cloning and chemical synthesis techniques. Such techniques include, but are not limited to nucleic acid amplification, e.g. polymerase chain reaction (PCR), with genomic DNA or cDNA targets using primers (e.g., a degenerate primer mixture) capable of annealing to antibody encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., microorganism, such as yeast or bacteria, a eukaryote such as an animal or mammalian cell or in a plant).

For expression or manipulation, nucleic acids can be incorporated into expression cassettes and vectors. Expression cassettes and vectors including a nucleic acid can be expressed when the nucleic acid is operably linked to an expression control element. As used herein, the term "operably linked" refers to a physical or a functional relationship between the elements referred to that permit them to operate in their intended fashion. Thus, an expression control element "operably linked" to a nucleic acid means that the control element modulates nucleic acid transcription and as appropriate, translation of the transcript.

Physical linkage is not required for the elements to be operably linked. For example, a minimal element can be linked to a nucleic acid encoding a glycogenic enzyme. A second element that controls expression of an operably linked nucleic acid encoding a protein that functions "in trans" to bind to the minimal element can influence expression of the glycogenic enzyme. Because the second element regulates expression of the glycogenic enzyme, the second element is operably linked to the nucleic acid encoding the glycogenic enzyme even though it is not physically linked.

The term "expression control element" refers to a nucleic acid that influences expression of an operably linked nucleic acid. Promoters and enhancers are particular non-limiting examples of expression control elements. A "promotor sequence" is a DNA regulatory region capable of initiating transcription of a downstream (3' direction) sequence. The promoter sequence includes nucleotides that facilitate transcription initiation. Enhancers also regulate gene expression, but can function at a distance from the transcription start site of the gene to which it is operably linked. Enhancers function at either 5' or 3' ends of the gene, as well as within the gene (e.g., in introns or coding sequences). Additional expression control elements include leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of interest, and stop codons.

Expression control elements include "constitutive" elements in which transcription of an operably linked nucleic acid occurs without the presence of a signal or stimuli. Expression control elements that confer expression in response to a signal or stimuli, which either increases or decreases expression of the operably linked nucleic acid, are "regulatable." A regulatable element that increases expression of the operably linked nucleic acid in response to a signal or stimuli is referred to as an "inducible element." A regulatable element that decreases expression of the operably linked nucleic acid in response to a signal or stimuli is referred to as a "repressible element" (i.e., the signal decreases expression; when the signal is removed or absent, expression is increased).

Expression control elements include elements active in a particular tissue or cell type, referred to as "tissue-specific expression control elements." Tissue-specific expression control elements are typically active in specific cell or tissue types because they are recognized by transcriptional activator proteins, or other regulators of transcription, that are active in the specific cell or tissue type as compared to other cell or tissue types.

For mammalian expression, constitutive promoters of viral or other origins may be used. For example, SV40, or viral long terminal repeats (LTRs) and the like, or inducible promoters derived from the genome of mammalian cells (e.g., metallothionein IIA promoter; heat shock promoter, steroid/thyroid hormone/retinoic acid response elements) or from mammalian viruses (e.g., the adenovirus late promoter; the inducible mouse mammary tumor virus LTR) are used.

The invention methods, inter alia, therefore include introducing nucleic acid or protein into target cells, e.g., cells of a subject, for treatment or prevention of Zika virus infection. Such cells are referred to as transformed cells. The term "transformed," when use in reference to a cell or organism, means a genetic change in a cell following incorporation of an exogenous molecule, for example, a protein or nucleic acid (e.g., a transgene) into the cell. Thus, a "transformed cell" is a cell into which, or a progeny of which an exogenous molecule has been introduced by the hand of man, for example, by recombinant DNA techniques. The nucleic acid or protein can be stably or transiently expressed in the transformed cell and progeny thereof. The transformed cell(s) can be propagated and the introduced protein expressed, or nucleic acid transcribed or encoded protein expressed. A progeny cell may not be identical to the parent cell, since there may be mutations that occur during replication.

Typically, cell transformation employs a "vector," which refers to a plasmid, virus, such as a viral vector, or other vehicle known in the art that can be manipulated by insertion or incorporation of a nucleic acid. For genetic manipulation "cloning vectors" can be employed, and to transcribe or translate the inserted polynucleotide "expression vectors" can be employed. Such vectors are useful for introducing nucleic acids, including nucleic acids that encode a glycogenic enzyme and nucleic acids that encode inhibitory nucleic acid, operably linked to an expression control element, and expressing the encoded protein or inhibitory nucleic acid (e.g., in solution or in solid phase), in cells or in a subject in vivo.

A vector generally contains an origin of replication for propagation in a cell. Control elements, including expression control elements as set forth herein, present within a vector, can be included to facilitate transcription and translation, as appropriate.

Vectors can include a selection marker. A "selection marker" is a gene that allows for the selection of cells containing the gene. "Positive selection" refers to a process in which cells that contain the selection marker survive upon exposure to the positive selection. Drug resistance is one example of a positive selection marker; cells containing the marker will survive in culture medium containing the selection drug, and cells lacking the marker will die. Selection markers include drug resistance genes such as neo, which confers resistance to G418; hygr, which confers resistance to hygromycin; and puro which confers resistance to puromycin. Other positive selection marker genes include genes that allow identification or screening of cells containing the marker. These genes include genes for fluorescent proteins (GFP and GFP-like chromophores, luciferase), the lacZ gene, the alkaline phosphatase gene, and surface markers such as CD8, among others. "Negative selection" refers to a process in which cells containing a negative selection marker are killed upon exposure to an appropriate negative selection agent. For example, cells which contain the herpes simplex virus-thymidine kinase (HSV-tk) gene (Wigler et al., Cell 11:223 (1977)) are sensitive to the drug gancyclovir (GANC). Similarly, the gpt gene renders cells sensitive to 6-thioxanthine.

Viral vectors included are those based on retroviral, adeno-associated virus (AAV), adenovirus, reovirus, lentivirus, rotavirus genomes, simian virus 40 (SV40) or bovine papilloma virus (Cone et al., Proc. Natl. Acad. Sci. USA 81:6349 (1984); Eukaryotic Viral Vectors, Cold Spring Harbor Laboratory, Gluzman ed., 1982; Sarver et al., Mol. Cell. Biol. 1:486 (1981)). Adenovirus efficiently infects slowly replicating and/or terminally differentiated cells and can be used to target slowly replicating and/or terminally differentiated cells. Additional viral vectors useful for expression include parvovirus, Norwalk virus, coronaviruses, paramyxo- and rhabdoviruses, togavirus (e.g., sindbis virus and semliki forest virus) and vesicular stomatitis virus (VSV).

Mammalian expression vectors include those designed for in vivo and ex vivo expression, such as AAV (U.S. Pat. No. 5,604,090). AAV vectors have previously been shown to provide expression in humans at levels sufficient for therapeutic benefit (Kay et al., Nat. Genet. 24:257 (2000); Nakai et al., Blood 91:4600 (1998)). Adenoviral vectors (U.S. Pat. Nos. 5,700,470, 5,731,172 and 5,928,944), herpes simplex virus vectors (U.S. Pat. No. 5,501,979) retroviral (e.g., lentivirus vectors are useful for infecting dividing as well as non-dividing cells and foamy viruses) vectors (U.S. Pat. Nos. 5,624,820, 5,693,508, 5,665,577, 6,013,516 and 5,674,703 and WIPO publications WO92/05266 and WO92/14829) and papilloma virus vectors (e.g., human and bovine papilloma virus) have all been employed in gene therapy (U.S. Pat. No. 5,719,054). Vectors also include cytomegalovirus (CMV) based vectors (U.S. Pat. No. 5,561,063). Vectors that efficiently deliver genes to cells of the intestinal tract have been developed (U.S. Pat. Nos. 5,821,235, 5,786,340 and 6,110,456).

A viral particle or vesicle containing the viral or mammalian vector can be designed to be targeted to particular cell types (e.g., undesirably proliferating cells) by inclusion of a protein on the surface that binds to a target cell ligand or receptor. Alternatively, a cell type-specific promoters and/or enhancer can be included in the vector in order to express the nucleic acid in target cells. Thus, the viral vector itself, or a protein on the viral surface can be made to target cells for transformation in vitro, ex vivo or in vivo.

Introduction of compositions (e.g., alpha-glucosidase inhibitory compounds, proteins, and nucleic acids) into target cells can also be carried out by methods known in the art such as osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylenevinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly(methylmethacrolate) microcapsules, respectively, or in a colloid system. Colloidal dispersion systems include macromolecule complexes, nano-capsules, microspheres, beads, and lipid-based systems, including oil-in-water emulsions, micelles, mixed micelles, and liposomes.

Liposomes for introducing various compositions into cells are known in the art and include, for example, phosphatidylcholine, phosphatidylserine, lipofectin and DOTAP (see, e.g., U.S. Pat. Nos. 4,844,904, 5,000,959, 4,863,740, and 4,975,282; and GIBCO-BRL, Gaithersburg, Md.). Piperazine based amphilic cationic lipids useful for gene therapy also are known (see, e.g., U.S. Pat. No. 5,861,397). Cationic lipid systems also are known (see, e.g., U.S. Pat. No. 5,459,127).

Polymeric substances, microcapsules and colloidal dispersion systems such as liposomes are collectively referred to herein as "vesicles." Accordingly, viral and non-viral vector means of delivery into cells or tissue, in vitro, in vivo and ex vivo are included.

The terms "protein," "polypeptide" and "peptide" are used interchangeably herein to refer to two or more covalently linked amino acids, or "residues," through an amide bond or equivalent. Polypeptides are not limited by length and the amino acids may be linked by non-natural and non-amide chemical bonds including, for example, those formed with glutaraldehyde, N-hydroxysuccinimide esters, bifunctional maleimides, or N,N'-dicyclohexylcarbodiimide (DCC). Non-amide bonds include, for example, ketomethylene, aminomethylene, olefin, ether, thioether and the like (see, e.g., Spatola in Chemistry and Biochemistry of Amino Acids, Peptides and Proteins, Vol. 7, pp 267-357 (1983), "Peptide and Backbone Modifications," Marcel Decker, NY).

The term "isolated," when used as a modifier of a composition, means that the compositions are made by the hand of man or are separated from their naturally occurring in vivo environment. Generally, compositions so separated are substantially free of one or more materials with which they normally associate with in nature, for example, one or more protein, nucleic acid, lipid, carbohydrate, cell membrane.

The term "isolated" does not exclude alternative physical forms, such as polypeptide multimers, post-translational modifications (e.g., phosphorylation, glycosylation) or derivatized forms.

An "isolated" composition can also be "substantially pure" when free of most or all of the materials with which it typically associates with in nature. Thus, an isolated molecule that also is substantially pure does not include polypeptides or polynucleotides present among millions of other sequences, such as antibodies of an antibody library or nucleic acids in a genomic or cDNA library, for example. A "substantially pure" molecule can be combined with one or more other molecules. Thus, the term "substantially pure" does not exclude combinations of compositions.

Substantial purity can be at least about 60% or more of the molecule by mass. Purity can also be about 70% or 80% or more, and can be greater, for example, 90% or more. Purity can be determined by any appropriate method, including, for example, UV spectroscopy, chromatography (e.g., HPLC, gas phase), gel electrophoresis (e.g., silver or coomassie staining) and sequence analysis (nucleic acid and peptide).

Nucleic acids, proteins, agents and other compositions useful in accordance with the invention include modified forms as set forth herein, provided that the modified form retains, at least a part of, a function or activity of the unmodified or reference nucleic acid, protein, agent or composition. For example, a nucleic acid encoding a modified protein that inhibits alpha-glucosidase activity can retain sufficient alpha-glucosidase inhibitory activity (the modified protein can be used alone or in combination with another agent that inhibits alpha-glucosidase activity), but have increased or decreased activity relative to a reference unmodified alpha-glucosidase inhibitor.

Thus, the invention further employs proteins, nucleic acids, compounds, agents and other compositions having modifications of the exemplary proteins, nucleic acids, compounds, agents and compositions. As used herein, the term "modify" and grammatical variations thereof, when used in reference to a composition such as a protein, nucleic acid, agent, or other composition means that the modified composition deviates from a reference composition. Such modified proteins, nucleic acids, agents and other compositions may have greater or less activity than a reference unmodified protein, nucleic acid, agent or composition.

Polypeptide modifications include amino acid substitutions, additions and deletions, which are also referred to as "variants." Polypeptide modifications also include one or more D-amino acids substituted for L-amino acids (and mixtures thereof), structural and functional analogues, for example, peptidomimetics having synthetic or non-natural amino acids or amino acid analogues and derivatized forms.

Polypeptide modifications further include fusion (chimeric) polypeptide sequences, which is an amino acid sequence having one or more molecules not normally present in a reference native (wild type) sequence covalently attached to the sequence, for example, one or more amino acids. Modifications include cyclic structures such as an end-to-end amide bond between the amino and carboxy-terminus of the molecule or intra- or inter-molecular disulfide bond. Polypeptides including antibodies may be modified in vitro or in vivo, e.g., post-translationally modified to include, for example, sugar residues, phosphate groups, ubiquitin, fatty acids or lipids.

A "conservative substitution" is the replacement of one amino acid by a biologically, chemically or structurally similar residue. Biologically similar means that the substitution is compatible with biological activity, e.g., enzyme activity or alpha-glucosidase inhibitory activity. Structurally similar means that the amino acids have side chains with similar length, such as alanine, glycine and serine, or having similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

The term "identical" or "identity" means that two or more referenced entities are the same. Thus, where two protein sequences are identical, they have the same amino acid sequence. An "area of identity" refers to a portion of two or more referenced entities that are the same. Thus, where two protein sequences are identical over one or more sequence regions they share amino acid identity in that region. The term "substantial identity" means that the molecules are structurally identical or have at least partial function of one or more of the functions (e.g., a biological function) of the reference molecule. Polypeptides having substantial identity include amino acid sequences with 50%, 60%, 70%, 75%, 80%, 85%, 90%, 95%, 96%, 97%, 98%, or more identity to a reference polypeptide, provided that modified polypeptide has at least partial activity, e.g., inhibits alpha-glucosidase production, accumulation or activity.

As used herein, the term "subsequence" or "fragment" means a portion of the full length molecule. A protein subsequence has one or more fewer amino acids than a full length comparison sequence (e.g., one or more internal or terminal amino acid deletions from either amino or carboxy-termini). A nucleic acid subsequence has at least one less nucleotide than a full length comparison nucleic acid sequence. Subsequences therefore can be any length up to the full length molecule.

Modified forms further include derivatized sequences, for example, amino acids in which free amino groups form amine hydrochlorides, p-toluene sulfonyl groups, carbobenzoxy groups; the free carboxy groups from salts, methyl and ethyl esters; free hydroxl groups that form O-acyl or O-alkyl derivatives, as well as naturally occurring amino acid derivatives, for example, 4-hydroxyproline, for proline, 5-hydroxylysine for lysine, homoserine for serine, ornithine for lysine, etc. Modifications can be produced using any of a variety of methods well known in the art (e.g., PCR based site-directed, deletion and insertion mutagenesis, chemical modification and mutagenesis, cross-linking, etc.).

Polypeptide sequences can be made using recombinant DNA technology of polypeptide encoding nucleic acids via cell expression or in vitro translation, or chemical synthesis of polypeptide chains using methods known in the art. Polypeptide sequences can also be produced by a chemical synthesizer (see, e.g., Applied Biosystems, Foster City, Calif.).

Compositions and Treatment

The alpha-glucosidase inhibitors of the present invention can be formulated into pharmaceutically acceptable salt forms or hydrate forms. Pharmaceutically acceptable salt forms include the acid addition salts and include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Pharmaceutically acceptable base addition salts include sodium, potassium, calcium, ammonium, and magnesium salts. Pharmaceutically acceptable salts of the polypeptides of the invention can be prepared using conventional techniques.

Administration of one or more glucosidase inhibitors can be carried out in the form of an oral tablet, capsule, or liquid formulation containing a therapeutically effective amount of the active ingredient (alpha-glucosidase inhibitor). Administration is not limited to oral delivery and includes intravascular (e.g., intravenous), intramuscular, or another means known in the pharmaceutical art for administration of active pharmaceutical ingredients.

The bioavailability of alpha-glucosidases varies. For example, castanospermine is a relatively polar molecule with potentially low oral bioavailability. The invention contemplates the optional use of methods to increase oral bioavailability of the alpha-glucosidase through use of a variety of permeability enhancers known in the art or prodrugs capable of decreasing the molecule's polarity to stimulate absorption. For example, the prodrug celgosivir (6-O-butanoyl castanospermine) readily crosses cell membranes and is rapidly converted by endogenous esterases to castanospermine (Kang (1996) *Glycobiology*, 6, 206-216). On those inhibitors with a free hydroxyl group on the molecule, phosphorylation of the hydroxyl group is one method that may be utilized to produce a prodrug. The alpha-glucosidase inhibitors, including prodrugs, and methods for their production are described in U.S. Pat. No. 5,043,273 (Scudder P R et al.) and incorporated herein by reference in their entirety.

Therapeutic or prophylactic application of the alpha-glucosidase inhibitors, and compositions containing them, can be accomplished by any suitable therapeutic or prophylactic method and technique presently or prospectively known to those skilled in the art. The inhibitors can be administered by any suitable route known in the art including, for example, oral, intramuscular, intraspinal, intracranial, nasal, rectal, parenteral, subcutaneous, or intravascular (e.g., intravenous) routes of administration. Administration of the alpha-glucosidase inhibitors of the invention can be continuous or at distinct intervals as can be readily determined by a person skilled in the art.

In some embodiments, an amount of inhibitor (e.g., 100 mg-1,000 mg) is to be administered 1, 2, 3, 4, or times per day, for 1, 2, 3, 4, 5, 6, 7, or more days. Treatment can continue as needed, e.g., for several weeks. Optionally, the treatment regimen can include a loading dose, with one or more daily maintenance doses. For example, in some embodiments, an initial loading dose in the range of 100 mg to 1,000 is administered, followed by a maintenance dose in the range of 100 mg to 1,000 mg every 12 hours for 1, 2, 3, 4, 5, 6, or 7, or more days. In some embodiments, an initial loading dose in the range of 200 mg to 600 mg is administered, followed by a maintenance dose in the range of 100 mg to 300 mg every 12 hours for a total of 9 doses.

Alpha-glucosidase inhibitors and compositions comprising them can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive inhibitor is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject inhibitors include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the inhibitors can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the total of one or more of the inhibitor based on the weight of the total composition including carrier or diluent.

The alpha-glucosidase inhibitors of the subject invention can also be administered utilizing liposome technology, slow release capsules, implantable pumps, and biodegradable containers. These delivery methods can, advantageously, provide a uniform dosage over an extended period of time.

The alpha-glucosidase inhibitors can also be modified by the addition of chemical groups, such as PEG (polyethylene glycol). PEGylated polypeptides typically generate less of an immunogenic response and exhibit extended half-lives in vivo in comparison to polypeptides that are not PEGylated when administered in vivo. Methods for PEGylating proteins and polypeptides known in the art (see, for example, U.S. Pat. No. 4,179,337). The subject polypeptides and polynucleotides can also be modified to improve cell membrane permeability. In one embodiment, cell membrane permeability can be improved by attaching a lipophilic moiety, such as a steroid, to the inhibitor. Other groups known in the art can be linked to the alpha-glucosidase inhibitors.

The subject invention also concerns a packaged dosage formulation comprising in one or more packages, packets, or containers at least one alpha-glucosidase inhibitor and/or composition of the subject invention formulated in a pharmaceutically acceptable dosage. The package can contain discrete quantities of the dosage formulation, such as tablet, capsules, lozenge, and powders. The quantity of alpha-glucosidase inhibitor in a dosage formulation and that can be administered to a patient can vary from about 1 mg to about 5000 mg, or about 1 mg to about 2000 mg, or more typically about 1 mg to about 500 mg, or about 5 mg to about 250 mg, or about 10 mg to about 100 mg. In some embodiments, the amount is in the range of 100 mg to 600 mg, to be administered 1, 2, 3, or 4 times per day, for 2, 3, 4, 5, 6, 7 or more days.

The subject invention also concerns kits comprising in one or more containers an alpha-glucosidase inhibitor of the present invention. A kit of the invention can also comprise one or more compounds, biological molecules, or drugs. In one embodiment, a kit of the invention can comprise an alpha-glucosidase inhibitor, and optionally comprises one or more of a drug or composition used in treating a viral infection (e.g., Zika virus infection).

Optionally, the methods further comprise, prior to administering the alpha-glucosidase inhibitor to the subject, identifying the subject as having a Zika virus infection or not having a Zika virus infection. If the subject is identified as having a Zika virus infection, the inhibitor can be administered as therapy. If the subject is identified as not having a Zika virus infection, the inhibitor can be withheld or administered as prophylaxis. The identifying step may comprise assaying a biological sample (e.g., blood, saliva, or urine) obtained from the subject for the presence of Zika virus nucleic acids or Zika virus proteins. In some embodiments, assaying includes the use of reverse transcriptase-polymerase chain reaction (RT-PCR), immunological assay (e.g., ELISA), or Plaque-reduction neutralization testing (PRNT).

Thus, optionally, the methods include, prior to administration of the alpha-glucosidase inhibitor, or re-administration of the alpha-glucosidase inhibitor, determining whether the subject has a Zika virus infection or one or more symptoms consistent with a Zika virus infection. During the first week after onset of symptoms, viral RNA can often be identified in serum; thus, Zika virus disease can be diagnosed by performing reverse transcriptase-polymerase chain reaction (RT-PCR) on serum. Urine and saliva samples may also be used for detection of Zika virus (Gourinat A-C et al. (2015) *Emerg Infect Dis*, vol. 21, no. 1, pp. 84-86; and Musso D et al. (2015) *J Clin Virol*, vol. 68, pp. 53-55).

Virus-specific IgM and neutralizing antibodies typically develop toward the end of the first week of illness; cross-reaction with related flaviviruses (e.g., dengue and yellow fever viruses) is common and may be difficult to discern. Plaque-reduction neutralization testing (PRNT) can be performed to measure virus-specific neutralizing antibodies and discriminate between cross-reacting antibodies in primary flavivirus infections.

Some individuals infected with Zika virus will not know they have the disease because they will not have symptoms. The most common symptoms of Zika virus infection are fever, maculo-papular rash (often spreading from face to body), joint pain, retro-orbital pain, or conjunctivitis (red eyes). Other common symptoms include general non-specific such as myalgia, asthenia, and headache. The incubation period (the time from exposure to symptoms) for Zika virus disease is not known, but is likely to be a few days to a week. The illness is usually mild with symptoms lasting for several days to a week after being bitten by an infected mosquito. The Zika virus usually remains in the blood of an infected person for approximately a week but it can be found longer in some individuals.

Treatment methods optionally include steps of advising that the subject get plenty of rest and drink fluids for hydration and administration of agents that alleviate symptoms of Zika virus infection, such as those that reduce fever and pain (e.g., acetaminophen and/or paracetamol). The methods may include administration of the fluids to the subject for hydration.

The subject may be any age or gender. In some embodiments, the subject is female. In some embodiments, the subject is a post-pubescent female. In some embodiments, the subject is a post-pubescent, pre-menopausal female. In some embodiments, the subject is a non-pregnant female. In some embodiments, the subject is a pregnant female.

In some embodiments, the subject has cancer at the time of administration of the alpha-glucosidase inhibitor. In other embodiments, the subject does not have cancer at the time of administration of the alpha-glucosidase inhibitor.

The invention further provides kits, including alpha-glucosidase inhibitors and pharmaceutical formulations, packaged into suitable packaging material, optionally in combination with instructions for using the kit components, e.g., instructions for performing a method of the invention. In one embodiment, a kit includes an amount of an alpha-glucosidase inhibitor, and instructions for administering the inhibitor to a subject in need of treatment on a label or packaging insert. In further embodiments, a kit includes an article of manufacture, for delivering the inhibitor into a subject locally, regionally or systemically, for example.

As used herein, the term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention, e.g., treating a Zika virus infection, an assay for identifying a subject having a Zika virus infection, etc. Thus, in additional embodiments, a kit includes a label or packaging insert including instructions for practicing a method of the invention in solution, in vitro, in vivo, or ex vivo.

Instructions can therefore include instructions for practicing any of the methods of the invention described herein. For example, pharmaceutical compositions can be included in a container, pack, or dispenser together with instructions for administration to a subject to treat a Zika virus infection. Instructions may additionally include appropriate administration route, dosage information, indications of a satisfactory clinical endpoint or any adverse symptoms that may occur, storage information, expiration date, or any information required by regulatory agencies such as the Food and Drug Administration or European Medicines Agency for use in a human subject.

The instructions may be on "printed matter," e.g., on paper or cardboard within the kit, on a label affixed to the kit or packaging material, or attached to a vial or tube containing a component of the kit. Instructions may comprise voice or video tape and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Kits can additionally include a buffering agent, a preservative, or an agent for stabilizing the alpha-glucosidase inhibitor. The kit can also include control components for assaying for the presence of Zika virus, e.g., a control sample or a standard. Each component of the kit can be enclosed within an individual container or in a mixture and all of the various containers can be within single or multiple packages.

Exemplified Embodiments

Embodiment 1. A method for treating or preventing Zika virus infection in a human or non-human animal subject, said method comprising administering an effective amount of an alpha-glucosidase inhibitor to a subject in need thereof.

Embodiment 2. The method of embodiment 1, wherein the alpha-glucosidase inhibitor comprises an alpha-glucosidase I inhibitor (also referred to as a glucosidase I inhibitor).

Embodiment 3. The method according to embodiment 1 or 2, wherein the subject has the Zika virus infection at the time of said administering.

Embodiment 4. The method according to any one of embodiments 1 to 3, further comprises, prior to said administering, identifying the subject as having the Zika virus infection.

Embodiment 5. The method according to embodiment 4, wherein said identifying comprises assaying a biological sample (e.g., blood, saliva, urine) obtained from the subject for the presence of Zika virus nucleic acids or Zika virus proteins.

Embodiment 6. The method according to embodiment 5, wherein said assaying comprises use of reverse transcriptase-polymerase chain reaction (RT-PCR), immunological assay (e.g., ELISA), or Plaque-reduction neutralization testing (PRNT).

Embodiment 7. The method according to embodiment 1 or 2, wherein the subject does not have the Zika virus infection at the time of said administering, and wherein the alpha-glucosidase inhibitor is administered as prophylaxis.

Embodiment 8. The method according to any one of embodiments 1 to 7, wherein the alpha-glucosidase inhibitor is administered orally, intravascularly (e.g., intravenously), nasally, rectally, parenterally, subcutaneously, or intramuscularly.

Embodiment 9. The method according to any one of embodiments 1 to 8, wherein the alpha-glucosidase inhibitor is one or more selected from among castanospermine, acarbose, miglitol voglibose, emiglitate, kotalanol, or a derivative or prodrug of any of the foregoing.

Embodiment 10. The method according to any one of embodiments 1 to 8, wherein the alpha-glucosidase inhibitor is castanospermine, or a derivative or prodrug thereof.

Embodiment 11. The method according to any one embodiments 1 to 8, wherein the alpha-glucosidase inhibitor is an alpha-glucosidase I inhibitor comprising castanospermine or celgosivir (6-O-butanoyl castanospermine).

Embodiment 12. The method according to embodiment 10 or 11, wherein the alpha-glucosidase inhibitor is administered orally or intravascularly (e.g., intravenously).

Embodiment 13. The method according to any one of embodiments 1 to 8, wherein the alpha-glucosidase inhibitor comprises a pseudoglucosylamine, such as validamine, valienamine, valiolamine, N-substituted valiolamine derivative, acarviosin derivative, acarbose, or higher pseudo-oligosaccharide.

Embodiment 14. The method according to any one of embodiments 1 to 8, wherein the alpha-glucosidase inhibitor comprises a polyhydroxypiperidine or polyhydroxypyrrolidine, such as nojirimycin, 1-deoxynojirimycin, N-substituted derivative of 1-deoxynojirimycin, branched and/or chain-extended deoxynojirimycin derivative (e.g., derivatives branched at C-1, branched at C-5, chain-extended at C-6), deoxy, amino, or halogen derivative, polyhydroxypiperidine with an altered configuration, bicyclic derivative of deoxynojirimycin (e.g., castanospermine, castanospermine derivative), or polyhydroxypyrrolidine (e.g., monocyclic pyrrolidine derivative or bicyclic pyrrolidine derivative).

Embodiment 15. The method according to any one of embodiments 1 to 8, wherein the alpha-glucosidase inhibitor is a biologic (e.g., polypeptide, nucleic acid molecule, antibody), or small molecule drug.

Embodiment 16. The method according to any one of embodiments 1 to 8, wherein the alpha-glucosidase inhibitor comprises an antisense molecule, small interfering RNA (siRNA), or ribozyme targeting alpha-glucosidase in the subject and inhibits alpha-glucosidase production.

Embodiment 17. The method according to any preceding embodiment, further comprising administering another agent for treating or preventing Zika virus, or a symptom thereof, in the same formulation as the alpha-glucosidase inhibitor, or in a separate formulation before, during, or after administration of the alpha-glucosidase inhibitor.

Embodiment 18. The method according to any one of embodiments 1 to 8, wherein the alpha-glucosidase inhibitor includes an attached group that enhances cellular uptake of alpha-glucosidase inhibitor.

Embodiment 19. The method according to any preceding embodiment, wherein the alpha-glucosidase inhibitor is encapsulated in a liposome.

Embodiment 20. The method according to any preceding embodiment, wherein the alpha-glucosidase inhibitor further includes an attached polyethylene glycol group.

Embodiment 21. The method according to any preceding embodiment, wherein the alpha-glucosidase inhibitor includes an attached lipophilic moiety that provides for improved cell membrane permeability.

Embodiment 22. The method according to any preceding embodiment, wherein the alpha-glucosidase inhibitor includes a permeability enhancer that decreases the alpha-glucosidase inhibitor's polarity to facilitate absorption.

Embodiment 23. A composition comprising an alpha-glucosidase inhibitor; and pharmaceutically acceptable buffer, carrier, or diluent.

Embodiment 24. The composition of embodiment 23, wherein the alpha-glucosidase inhibitor comprises an alpha-glucosidase I inhibitor (also referred to as a glucosidase I inhibitor).

Embodiment 25. The composition of embodiment 24, wherein the alpha-glucosidase inhibitor is one or more selected from among castanospermine, acarbose, miglitol voglibose, emiglitate, kotalanol, or a derivative or prodrug of any of the foregoing.

Embodiment 26. The composition of embodiment 24, wherein the alpha-glucosidase inhibitor is castanospermine, or a derivative or prodrug thereof.

Embodiment 27. The composition of embodiment 24, wherein the alpha-glucosidase inhibitor is an alpha-glucosidase I inhibitor comprising castanospermine or celgosivir (6-O-butanoyl castanospermine).

Embodiment 28. The composition of embodiment 24, wherein the alpha-glucosidase inhibitor comprises a pseudoglucosylamine, such as validamine, valienamine, valiolamine, N-substituted valiolamine derivative, acarviosin derivative, acarbose, or higher pseudo-oligosaccharide.

Embodiment 29. The composition of embodiment 24, wherein the alpha-glucosidase inhibitor comprises a polyhydroxypiperidine or polyhydroxypyrrolidine, such as nojirimycin, 1-deoxynojirimycin, N-substituted derivative of 1-deoxynojirimycin, branched and/or chain-extended deoxynojirimycin derivative (e.g., derivatives branched at C-1, branched at C-5, chain-extended at C-6), deoxy, amino, or halogen derivative, polyhydroxypiperidine with an altered configuration, bicyclic derivative of deoxynojirimycin (e.g., castanospermine, castanospermine derivative), or polyhydroxypyrrolidine (e.g., monocyclic pyrrolidine derivative or bicyclic pyrrolidine derivative).

Embodiment 30. The composition of embodiment 24, wherein the alpha-glucosidase inhibitor is a biologic (e.g., polypeptide, nucleic acid molecule, antibody), or small molecule drug.

Embodiment 31. The composition of embodiment 24, wherein the alpha-glucosidase inhibitor comprises an antisense molecule, small interfering RNA (siRNA), or ribozyme targeting alpha-glucosidase in the subject and inhibits alpha-glucosidase production.

Embodiment 32. The composition of any one of embodiments 24 to 31, further comprising an additional agent effective for the treatment or prevention of Zika virus infection.

Embodiment 33. The composition of any one of embodiments 24 to 32, further comprising an additional agent effective for the treatment of one or more symptoms of Zika virus infection.

Embodiment 34. The composition of any one of embodiments 24 to 33, wherein the alpha-glucosidase inhibitor includes an attached group that enhances cellular uptake of alpha-glucosidase inhibitor.

Embodiment 35. The composition of any one of embodiments 24 to 34, wherein the alpha-glucosidase inhibitor is encapsulated in a liposome.

Embodiment 36. The composition of any one of embodiments 24 to 35, wherein the alpha-glucosidase inhibitor further includes an attached polyethylene glycol group.

Embodiment 37. The composition of any one of embodiments 24 to 36, wherein the alpha-glucosidase inhibitor includes an attached lipophilic moiety that provides for improved cell membrane permeability.

Embodiment 38. The composition of any one of embodiments 24 to 37, wherein the alpha-glucosidase inhibitor includes a permeability enhancer that decreases the alpha-glucosidase inhibitor's polarity to facilitate absorption.

Embodiment 39. A packaged dosage formulation comprising at least one alpha-glucosidase inhibitor in a pharmaceutically acceptable dosage in one or more packages, packets, or containers.

Embodiment 40. The packaged dosage formulation of embodiment 39, wherein the alpha-glucosidase inhibitor comprises an alpha-glucosidase I inhibitor (also referred to as a glucosidase I inhibitor).

Embodiment 41. The packaged dosage formulation of embodiment 40, wherein the alpha-glucosidase inhibitor is one or more selected from among castanospermine, acarbose, miglitol voglibose, emiglitate, kotalanol, or a derivative or prodrug of any of the foregoing.

Embodiment 42. The packaged dosage formulation of embodiment 40, wherein the alpha-glucosidase inhibitor is castanospermine, or a derivative or prodrug thereof.

Embodiment 43. The packaged dosage formulation of embodiment 40, wherein the alpha-glucosidase inhibitor comprises castanospermine or celgosivir (6-O-butanoyl castanospermine).

Embodiment 44. The packaged dosage formulation of embodiment 39, wherein the alpha-glucosidase inhibitor comprises a pseudoglucosylamine, such as validamine, valienamine, valiolamine, N-substituted valiolamine derivative, acarviosin derivative, acarbose, or higher pseudo-oligosaccharide.

Embodiment 45. The packaged dosage formulation of embodiment 39, wherein the alpha-glucosidase inhibitor comprises a polyhydroxypiperidine or polyhydroxypyrrolidine, such as nojirimycin, 1-deoxynojirimycin, N-substituted derivative of 1-deoxynojirimycin, branched and/or chain-extended deoxynojirimycin derivative (e.g., derivatives branched at C-1, branched at C-5, chain-extended at C-6), deoxy, amino, or halogen derivative, polyhydroxypiperidine with an altered configuration, bicyclic derivative of deoxynojirimycin (e.g., castanospermine, castanospermine derivative), or polyhydroxypyrrolidine (e.g., monocyclic pyrrolidine derivative or bicyclic pyrrolidine derivative).

Embodiment 46. The packaged dosage formulation of embodiment 39, wherein the alpha-glucosidase inhibitor is a biologic (e.g., polypeptide, nucleic acid molecule, antibody), or small molecule drug.

Embodiment 47. The packaged dosage formulation of embodiment 39, wherein the alpha-glucosidase inhibitor comprises an antisense molecule, small interfering RNA (siRNA), or ribozyme targeting alpha-glucosidase in the subject and inhibits alpha-glucosidase production.

Embodiment 48. The packaged dosage formulation of embodiment 39, wherein said at least one alpha-glucosidase is provided as a tablet, capsule, lozenge, liquid, or powder.

Embodiment 49. The packaged dosage formulation of embodiment 39, further comprising an additional agent effective for the treatment or prevention of Zika virus infection.

Embodiment 50. The packaged dosage formulation of any one of embodiments 39 to 48, further comprising an additional agent effective for the treatment of one or more symptoms of Zika virus infection.

Embodiment 51. The packaged dosage formulation of any one of embodiments 39 to 49, wherein the alpha-glucosidase inhibitor includes an attached group that enhances cellular uptake of alpha-glucosidase inhibitor.

Embodiment 52. The packaged dosage formulation of any one of embodiments 39 to 51, wherein the alpha-glucosidase inhibitor is encapsulated in a liposome.

Embodiment 53. The packaged dosage formulation of any one of embodiments 39 to 52, wherein the alpha-glucosidase inhibitor further includes an attached polyethylene glycol group.

Embodiment 54. The packaged dosage formulation of any one of embodiments 39 to 53, wherein the alpha-glucosidase inhibitor includes an attached lipophilic moiety that provides for improved cell membrane permeability.

Embodiment 55. The packaged dosage formulation of any one of embodiments 39 to 54, wherein the alpha-glucosidase inhibitor includes a permeability enhancer that decreases the alpha-glucosidase inhibitor's polarity to facilitate absorption.

Embodiment 56. A kit comprising, in one or more containers, an alpha-glucosidase inhibitor.

Embodiment 57, wherein the alpha-glucosidase inhibitor comprises an alpha-glucosidase I inhibitor (also referred to as a glucosidase I inhibitor).

Embodiment 58. The kit of embodiment 56 or 57, further comprising instructions for administration of the alpha-glucosidase inhibitor for the treatment or prevention of Zika virus infection.

Embodiment 59. The kit of one of embodiments 56 to 58, wherein the alpha-glucosidase inhibitor is one or more selected from among castanospermine, acarbose, miglitol voglibose, emiglitate, kotalanol, or a derivative or prodrug of any of the foregoing.

Embodiment 60. The kit of any one of embodiments 56 to 58, wherein the alpha-glucosidase inhibitor is castanospermine, or a derivative or prodrug thereof.

Embodiment 61. The kit of any one of embodiments 56 to 58, wherein the alpha-glucosidase inhibitor comprises castanospermine or celgosivir (6-O-butanoyl castanospermine).

Embodiment 62. The kit of embodiment 56, wherein the alpha-glucosidase inhibitor comprises a pseudoglucosylamine, such as validamine, valienamine, valiolamine, N-substituted valiolamine derivative, acarviosin derivative, acarbose, or higher pseudo-oligosaccharide.

Embodiment 63. The kit of embodiment 56 or 58, wherein the alpha-glucosidase inhibitor comprises a polyhydroxypiperidine or polyhydroxypyrrolidine, such as nojirimycin, 1-deoxynojirimycin, N-substituted derivative of 1-deoxynojirimycin, branched and/or chain-extended deoxynojirimycin derivative (e.g., derivatives branched at C-1, branched at C-5, chain-extended at C-6), deoxy, amino, or halogen derivative, polyhydroxypiperidine with an altered configuration, bicyclic derivative of deoxynojirimycin (e.g., castanospermine, castanospermine derivative), or polyhydroxypyrrolidine (e.g., monocyclic pyrrolidine derivative or bicyclic pyrrolidine derivative).

Embodiment 64. The kit of any one of embodiments 56 to 58, wherein the alpha-glucosidase inhibitor is a biologic (e.g., polypeptide, nucleic acid molecule, antibody), or small molecule drug.

Embodiment 65. The kit of embodiment 56 or 64, wherein the alpha-glucosidase inhibitor comprises an antisense molecule, small interfering RNA (siRNA), or ribozyme targeting alpha-glucosidase in the subject and inhibits alpha-glucosidase production.

Embodiment 66. The kit of any one of embodiments 56 to 65, further comprising an additional agent effective for the treatment or prevention of Zika virus infection.

Embodiment 67. The kit of any one of embodiments 56 to 66, further comprising an additional agent effective for the treatment of one or more symptoms of Zika virus infection.

Embodiment 68. The kit of any one of embodiments 56 to 67, wherein the alpha-glucosidase inhibitor includes an attached group that enhances cellular uptake of alpha-glucosidase inhibitor.

Embodiment 69. The kit of any one of embodiments 56 to 68, wherein the alpha-glucosidase inhibitor is encapsulated in a liposome.

Embodiment 70. The kit of any one of embodiments 56 to 69, wherein the alpha-glucosidase inhibitor further includes an attached polyethylene glycol group.

Embodiment 71. The kit of any one of embodiments 56 to 70, wherein the alpha-glucosidase inhibitor includes an attached lipophilic moiety that provides for improved cell membrane permeability.

Embodiment 72. The kit of any one of embodiments 56 to 71, wherein the alpha-glucosidase inhibitor includes a permeability enhancer that decreases the alpha-glucosidase inhibitor's polarity to facilitate absorption.

DEFINITIONS

As used herein, a subject is "in need of" a treatment if such human or non-human animal subject would benefit biologically, medically or in quality of life from such treatment (preferably, a human). In some embodiments, the subject has a Zika virus infection and is in need of therapy. In other embodiments, the subject does not have a Zika virus infection and is in need of prophylaxis. In some embodiments, the subject in need of prophylaxis is at risk of becoming infected with the Zika virus. In some embodiments, the subject is at increased risk of becoming infected with the Zika virus relative to others in the population.

As used herein, the terms "subject", "patient", and "individual" refer to a human or non-human animal. Typically, the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the subject. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to prophylaxis (preventing or delaying the onset or development or progression of the disease or disorder).

As used herein, the term "administration" is intended to include, but is not limited to, the following delivery methods: topical, oral, parenteral, subcutaneous, transdermal, transbuccal, intravascular (e.g., intravenous or intra-arterial), intramuscular, subcutaneous, intranasal, and intra-ocular administration. Administration can be local at a particular anatomical site, such as a site of infection, or systemic.

As used herein, the term "contacting" in the context of contacting a cell with at least one alpha-glucosidase inhibitor in vitro or in vivo means bringing at least one inhibitor into contact with the cell, or vice-versa, or any other manner of causing the inhibitor and the cell to come into contact.

The compounds of the present invention can be formulated into pharmaceutically-acceptable salt forms. Pharmaceutically-acceptable salts of the compounds of the invention can be prepared using conventional techniques. "Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, a "derivative" or "pharmaceutically active derivative" refers to any compound that upon administration to the recipient, is capable of providing directly or indirectly, the activity disclosed herein (e.g., anti-Zika virus activity and/or alpha-glucosidase inhibitory activity, such as inhibition of alpha-glucosidase I). The term "indirectly" also encompasses "prodrugs" which may be converted to the active form of the drug, e.g., via endogenous enzymes or metabolism (biotransformation). The prodrug is a derivative of the compounds according to the invention and presenting alpha-glucosidase inhibitory activity (e.g., alpha-glucosidase I inhibitory activity) that has a chemically or metabolically decomposable group, and a compound that may be converted into a pharmaceutically active compound according to the invention in vivo by solvolysis under physiological conditions. The prodrug is converted into a compound according to the present invention by a reaction with an enzyme, gastric acid or the like under a physiological condition in the living body, e.g., by oxidation, reduction, hydrolysis or the like, each of which is carried out enzymatically. These compounds can be produced from compounds of the present invention according to well-known methods. The term "indirectly" also encompasses metabolites of compounds according to the invention. Chemical reactions, reactants, and reagents useful for making derivatives can be found, for example, in *March's Advanced Organic Chemistry*, 7$^{th}$ edition, 2013, Michael B. Smith, which is incorporated herein by reference in its entirety.

More specifically, the term "prodrug" refers to a chemical compound that can be converted by the body (i.e., biotransformed) to another chemical compound that has pharmacological activity. The prodrug may itself have pharmacological activity before conversion, or be inactive before conversion and activated upon conversion. Active prodrugs or inactive prodrugs of compounds of the invention may be administered to a subject or contacted with a cell in vitro or in vivo. Instead of administering a drug directly, a prodrug may be used instead to improve how a drug is absorbed, distributed, metabolized, and excreted (ADME). For example, a prodrug may be used to improve bioavailability when a drug itself is poorly absorbed from the gastrointestinal tract, or to improve how selectively the drug interacts with cells or processes that are not its intended target, which can reduce adverse or unintended effects of a drug. Major types of prodrugs include, but are not limited to, type I prodrugs, which are biotransformed inside cells (intracellularly), and type II prodrugs, which are biotransformed outside cells (extracellularly), such as in digestive fluids or in the body's circulatory system. These types can be further categorized into subtypes based on factors such as whether the intracellular bioactivation location is also a site of therapeutic action, or whether or not bioactivation occurs in the gastrointestinal fluids or in the circulation system (Wu, Kuei-Meng, "A New Classification of Prodrugs: Regulatory Perspectives, *Pharmaceuticals,* 2009, 2(3):77-81, which is incorporated by reference herein in its entirety).

The term "metabolite" refers to all molecules derived from any of the compounds according to the present invention in a cell or organism, preferably mammal. Pharmaceutically active metabolites of the compounds of the invention may be administered to a subject or contacted with a cell in vitro or in vivo.

The phrase "pharmaceutically acceptable" indicates that the substance or composition must be compatible chemically and/or toxicologically, with the other ingredients comprising a formulation, and/or the mammal being treated therewith.

Pharmaceutical formulations include "pharmaceutically acceptable" and "physiologically acceptable" carriers, diluents or excipients. In this context, the terms "pharmaceutically acceptable" and "physiologically acceptable" include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or microbead. Supplementary compounds (e.g., preservatives, antibacterial, antiviral and antifungal agents) can also be incorporated into the compositions.

The phrase "effective amount" means an amount of an agent, such as an alpha-glucosidase inhibitor, that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

As used herein, a subject is "in need of" a treatment if such human or non-human animal subject would benefit biologically, medically or in quality of life from such treatment (preferably, a human).

As used herein, the term "inhibit", "inhibition" or "inhibiting" refers to the reduction or suppression of a given condition, symptom, or disorder, or disease (e.g., Zika virus infection, or Zika viral load or titer), or a significant decrease in the baseline activity of a biological activity or process (e.g., alpha-glucosidase production, inhibitors of glycoprotein processing, and inhibitors of alpha-glucosidase activity such as alpha-glucosidase I activity).

The terms "compounds of the present invention" or "agents of the invention" (unless specifically identified otherwise) refer to alpha-glucosidase inhibitors including salts thereof, as well as all stereoisomers (including diastereoisomers and enantiomers), rotamers, tautomers and isotopically labeled compounds (including deuterium substitutions), as well as inherently formed moieties (e.g., polymorphs, solvates and/or hydrates). For purposes of this invention, solvates and hydrates are generally considered compositions.

The term "a," "an," "the" and similar terms used in the context of the present invention (especially in the context of the claims) are to be construed to cover both the singular and plural unless otherwise indicated herein or clearly contradicted by the context. For example, the term "cell" includes a singular cell and a plurality of cells unless specified to the contrary; and the term "inhibitor" includes a singular inhibitor and a plurality of inhibitors.

EXAMPLE 1

Anti-Zika Virus Activity of Castanospermine in SNB-19 Cells

Using ZIKV protein NS1 expression as a read-out for anti-ZIKV activity, the alpha-glucosidase inhibitor castanospermine was tested and found to significantly inhibit ZIKV infection in SNB-19 cells. Cells of the glioblastoma SNB-19 cell line were maintained at 37° C. in 5% $CO_2$ in RPMI-60, 1× penicillin/streptomycin, and 10% fetal bovine serum (Invitrogen). SNB-19 cells were treated with castanospermine at increasing concentrations (100 μm, 500 μm, and 1 mM) one hour prior to inoculation with the FSS-13025 strain of ZIKV. Cells were harvested 24 hours post-infection and analyzed by Western blot for ZIKV-NS1 or GAPDH. Results are shown in FIG. 1.

EXAMPLE 2

Anti-Zika Virus Activity of Castanospermine in Ifnar 1−/− Mouse Model

Ifnar 1−/− mice (C57BL/6 background) were obtained (Muller U. et al. "Functional role of type I and type II interferons in antiviral defense". *Science*. 1994; 264(5167): 1918-21. Epub 1994/06/24). Out of 18 total Ifnar 1−/− mice, two mice were dosed with castanospermine and media, 8 mice (male+female) were dosed with saline and ZIKV, and 8 mice were dosed with castanospermine and ZIKV on day-0. The drug was continued for three more days and animals were sacrificed on day-3. Body weight and water consumption were monitored daily. The experiment protocol is summarized in Tables 1 and 2.

Figures 3A, 3B:
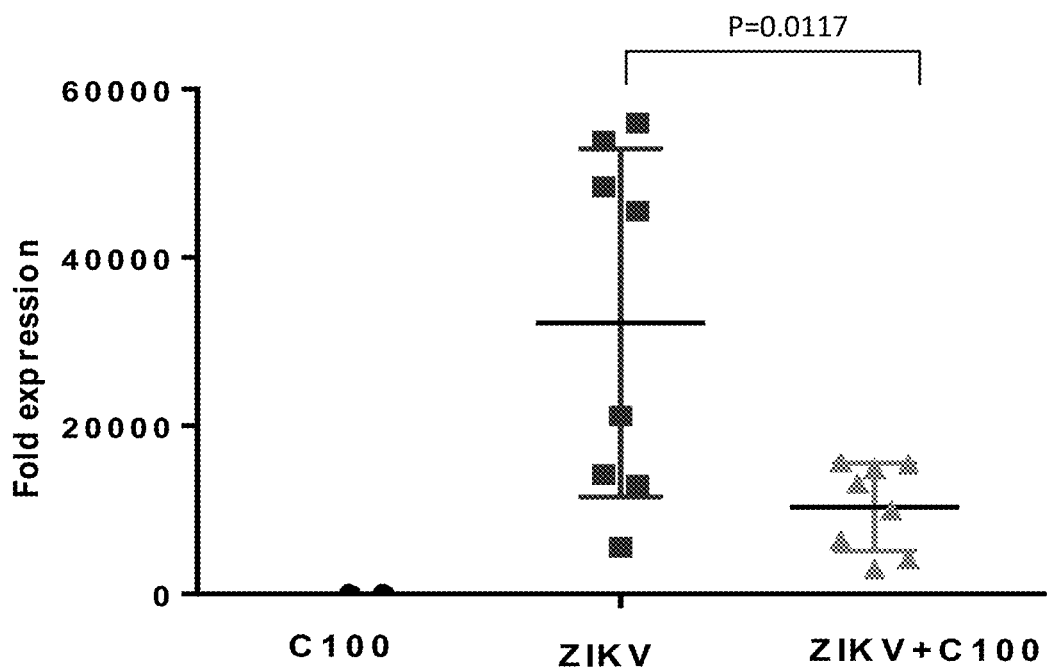
FIGS. 3A-3B. Zika viral load in liver of Ifnar 1−/− mice. After euthanizing the mice, liver tissue samples were stored in RNAase later buffer, and after homogenization in lysis buffer the total RNA was extracted using Rneasy column (Qiagen). cDNA was prepared using RT reaction. The expression level of the ZIKV NS1 gene was quantified by real time PCR using specific primers. Statistical analysis was done by unpaired t-test using GraphPad Prism software. *$p<0.05$ is considered as significant (FIG. 3B). There was a 68% decrease in the viral load in the liver with castanospermine treatment (FIG. 3A).
Figure 4:
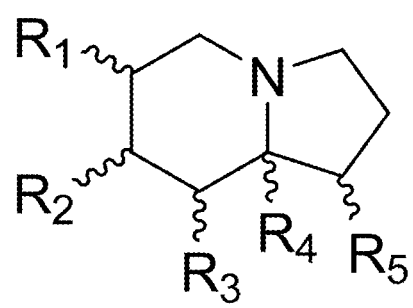
FIG. 4. Chemical structure illustrating an embodiment of alpha-glucosidase I inhibitors (also referred to as glucosidase I inhibitors). The structure of FIG. 4 encompasses castanospermine and some derivatives of castanospermine.
Figure 5:
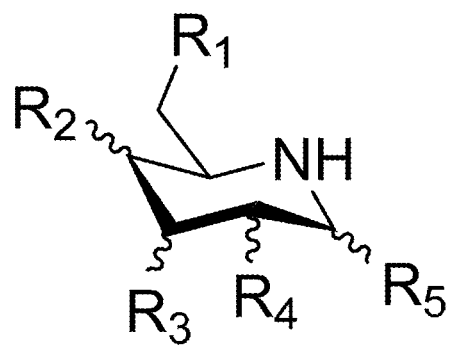
FIG. 5. Chemical structure illustrating an embodiment of alpha-glucosidase I inhibitors (also referred to as glucosidase I inhibitors). The structure of FIG. 5 encompasses nojirimycin and some derivatives of nojirimycin.

Results are shown in FIGS. 2A-2B and 3A-3B. With castanospermine treatment, there was 46% reduction in Zika virus load as estimated by NS1 protein in the serum (FIG. 2A). There was a 68% decrease in the viral load in the liver with castanospermine treatment (FIG. 3A).

TABLE 1

| | |
|---|---|
| Drug | Castanospermine (100 mg/kg BW) |
| Route of administration of drug | Intraperitoneal (in Saline) |
| Route of Zika virus challenge | Intraperitoneal (FSS13025) |
| Duration of study | 3 days |
| FSU ACUC approval | Protocol #1621 |

TABLE 2

| ZIKV NS1 ELISA | | | |
|---|---|---|---|
| Day 0 | Day 1 | Day 2 | Day 3 |
| Casta | Casta | Casta | Casta |

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method for treating or delaying the onset of Zika virus infection in a human or non-human animal subject, said method comprising administering an effective amount of an alpha-glucosidase inhibitor to a subject in need thereof, wherein the alpha-glucosidase inhibitor comprises castanospermine, or a pharmaceutically acceptable salt, derivative, or prodrug thereof.

2. The method of claim 1, wherein the subject has the Zika virus infection at the time of said administering.

3. The method of claim 2, further comprising, prior to said administering, identifying the subject as having the Zika virus infection.

4. The method of claim 3, wherein said identifying comprises assaying a biological sample obtained from the subject for the presence of Zika virus nucleic acids or Zika virus proteins.

5. The method of claim 4, wherein said assaying comprises use of reverse transcriptase-polymerase chain reaction (RT-PCR), immunological assay, or Plaque-reduction neutralization testing (PRNT).

6. The method of claim 1, wherein the subject does not have the Zika virus infection at the time of said administering and the alpha-glucosidase inhibitor is administered as prophylaxis.

7. The method of claim 1, wherein the alpha-glucosidase inhibitor is administered orally, intravascularly, nasally, rectally, parenterally, subcutaneously, or intramuscularly.

8. The method of claim 1, wherein the alpha-glucosidase I inhibitor comprises castanospermine, or a pharmaceutically acceptable salt thereof.

9. The method of claim 1, wherein the derivative or prodrug is administered to the subject, and the derivative or prodrug comprises celgosivir (6-O-butanoyl castanospermine) or a pharmaceutically acceptable salt thereof.

10. The method of claim 1, wherein the alpha-glucosidase is administered orally or intravenously.

11. The method of claim 1, further comprising administering another agent for treating or delaying onset Zika virus infection, or a symptom thereof, in the same formulation as the alpha-glucosidase inhibitor, or in a separate formulation before, during, or after administration of the alpha-glucosidase inhibitor.

12. The method of claim 1, wherein the alpha-glucosidase inhibitor includes an attached group that enhances cellular uptake of the alpha-glucosidase inhibitor.

13. The method of claim 1, wherein the alpha-glucosidase inhibitor is encapsulated in a liposome.

14. The method of claim 1, wherein the alpha-glucosidase inhibitor further includes an attached polyethylene glycol group.

15. The method of claim 1, wherein the alpha-glucosidase inhibitor includes an attached lipophilic moiety that provides for improved cell membrane permeability.

16. The method of claim 1, wherein the alpha-glucosidase inhibitor includes a permeability enhancer that decreases the alpha-glucosidase inhibitor's polarity to facilitate absorption.

17. The method of claim 1, wherein the subject is a human.

18. The method of claim 1, wherein the subject is a non-human animal.

19. The method of claim 1, wherein the subject is a mammal.

20. A method for inhibiting a Zika virus infection in a cell, comprising contacting the infected cell with an alpha-glucosidase inhibitor in vivo, wherein the alpha-glucosidase inhibitor comprises castanospermine, or a pharmaceutically acceptable salt, derivative, or prodrug thereof.

* * * * *